United States Patent
Boden et al.

(10) Patent No.: US 6,689,290 B2
(45) Date of Patent: Feb. 10, 2004

(54) FAMILY OF CONDUCTING LIQUID CRYSTALS

(75) Inventors: Neville Boden, Leeds (GB); Richard James Bushby, Leeds (GB); Gareth Headdock, North Yorkshire (GB); Owen Roger Lozman, Leeds (GB); Andrew Wood, Liverpool (GB); Ekaterina Olegovna Arikanien, Derbyshire (GB); Andrew Paul McNeill, Plymouth (GB); Zhibao Lu, Leeds (GB); Quayling Liu, Leeds (GB)

(73) Assignee: The University of Leeds, Leeds (GB)

( * ) Notice: Subject to any disclaimer, the term of this patent is extended or adjusted under 35 U.S.C. 154(b) by 0 days.

(21) Appl. No.: 10/149,460
(22) PCT Filed: Dec. 8, 2000
(86) PCT No.: PCT/GB00/04691
§ 371 (c)(1), (2), (4) Date: Jan. 13, 2003
(87) PCT Pub. No.: WO01/42391
PCT Pub. Date: Jun. 14, 2001

(65) Prior Publication Data
US 2003/0160212 A1 Aug. 28, 2003

(30) Foreign Application Priority Data
Dec. 8, 1999 (GB) .............................................. 9928883

(51) Int. Cl.$^7$ ............................................... C09K 19/06
(52) U.S. Cl. ............................... 252/299.6; 252/299.61; 252/299.62; 252/299.01; 544/343; 585/26; 546/70; 568/632; 532/1
(58) Field of Search ............. 252/299.01, 299.61, 252/299.62, 299.63, 299.64, 299.6; 544/343; 585/26; 546/70; 568/632; 532/1

(56) References Cited

FOREIGN PATENT DOCUMENTS

JP 11092420 4/1999

OTHER PUBLICATIONS

Arikainen et al., "Complimentary Polytopic Interactions" *Angewandte Chemi, Int. Ed.* 39(13):2333–2336. (2000).
Baxter, Paul N.W. et al. "The Designed Self–Assembly of Multicomponent and Multicompartmental Cylindrical Nanoarchitectures" *Chem. Eur. J.* 5(1):113–120 (1999).
Baxter, Paul N.W. et al. "The Design and Generation of Inorganic Cylindrical Cage Architectures by Metal–Ion–Directed Multicomponent Self–Assembly" *Chem. Eur. J.* 5(1):113–120 (1999).
Boden et al. "Cyano Substituted Triphenylene–based Discotic Mesogens" *Liquid Crystals.* 26(4):495–499 (1999).

(List continued on next page.)

Primary Examiner—Mark F. Huff
Assistant Examiner—Jennifer R Sadula
(74) Attorney, Agent, or Firm—Myers Bigel Sibley & Sajovec PA

(57) ABSTRACT

A mixture comprising a molecule of formula (I); in which $A_1$, $A_2$, $A_3$, $A_4$, $A_5$ and $A_6$, which may be the same or different, are each N or —CH; $Y_1$, $Y_2$, $Y_3$, $Y_4$, $Y_5$ and $Y_6$, which may be the same or different, are each hydrogen or $C_1$ to $C_{12}$ alkoxy; $X_1$, $X_2$, $X_3$, $X_4$, $X_5$ and $X_6$, which may be the same or different, are each hydrogen, $C_1$ to $C_{12}$ alkoxy or alkyl $C_1$ to $C_{12}$; and $R_7$, $R_8$, $R_9$, $R_{10}$, $R_{11}$ and $R_{12}$ are each hydrogen, or each of $R_7$ and $R_8$, $R_9$ and $R_{10}$ and $R_{11}$ and $R_{12}$ may form a bond; and a molecule of formula (II); in which $R_1$, $R_2$, $R_3$, $R_4$, $R_5$ and $R_6$, which may be the same or different, are each alkyl or substituted (and/or chiral) alkyl $C_1$ to $C_{16}$, acyl $C_1$ to $C_{16}$, polyethyleneoxy, a flexible connection to a polymer backbone or part of a polymer backbone in homopolymers, copolymers or block copolymers; and $B_1$, $B_2$, $B_3$, $B_4$, $B_5$ and $B_6$a, which may be the same or different, are each, hydrogen, alkyl $C_1$ to $C_{16}$, alkoxy $C_1$ to $C_{16}$, nitro, halogeno, cyano, amido, diazo or ester, e.g. alkyl $C_1$ to $C_{16}$ ester.

55 Claims, 5 Drawing Sheets

Phase composition diagram for binary mixtures of 2,3,6,7,10,11 hexahexyloxy triphenylene and 2,3,6,7,10,11-hexakis(4-n-nonylphenyl)dipyrazine[2,3-f:2',3'-h]quinoxaline;

OTHER PUBLICATIONS

Demus, et al. *Handbook of Liquid Crystals*. vol. 2B pp. 702–712. (1998).

International Search Report corresponding to PCT/GB00/04691 mailed on Aug. 28, 2001.

Kohne, Bernd and Klaus Praefcke, "A New and Simple Synthesis of the Dipyrazino[2,3–f:2',3'–h]quinoxaline Ring System" *Liebigs Ann. Chem.* 522–528 (1985). (Abstract only in English).

Radler, Sonja and Albert Hasper. "Evaluation of a Novel Twin 300mm Furnace Concept for High Productivity in a Pilot Production".

Yatabe, et al. "Extended Triphenylenes: Synthesis, Mesomorphic Properties and Molecularly Resolved Scanning Tunneling Microscopy Images of Hexakis(dialkoxypheny) triphenylese and Dodeca(alkoxy)tris(triphenylenylenes)s" *J. Mater. Chem.* 10:1519–1525. (2000).

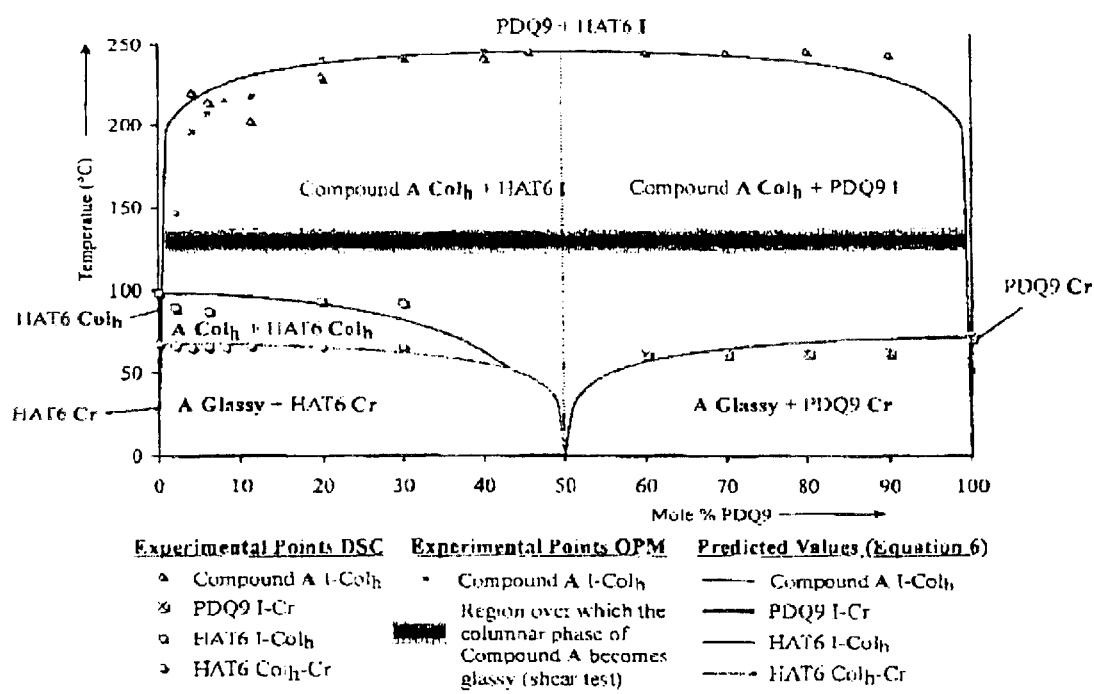
Figure 1 : Phase composition diagram for binary mixtures of 2,3,6,7,10,11 hexahexyloxy triphenylene and 2,3,6,7,10,11-hexakis(4-n-nonylphenyl)dipyrazine[2,3-f:2',3'-h]quinoxaline;

Figure 2 : The optical texture of the polymer with formula VII (n=12). Left shows the polymer alone upon cooling from the melt. Right shows the optical texture of the compound formed by the mixture of polymer with formula VII (n=12) and 2,3,6,7,10,11-hexakis(4-n-nonylphenyl)dipyrazine[2,3-f:2',3'-h]quinoxaline.

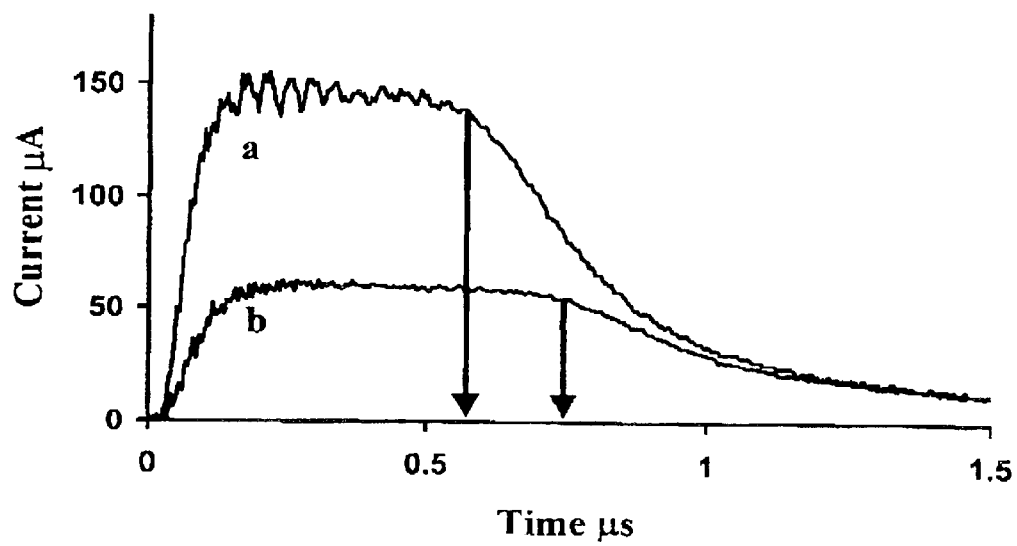
Figure 3. A typical time of flight photocurrent transient is shown for holes in the HAT11:PTP9 mix in a) the discotic mesophase and b) in the glassy phase. The electric field is $E = 3.88 MVm^{-1}$ and the temperature $T = 393K$. The transit time is indicated.

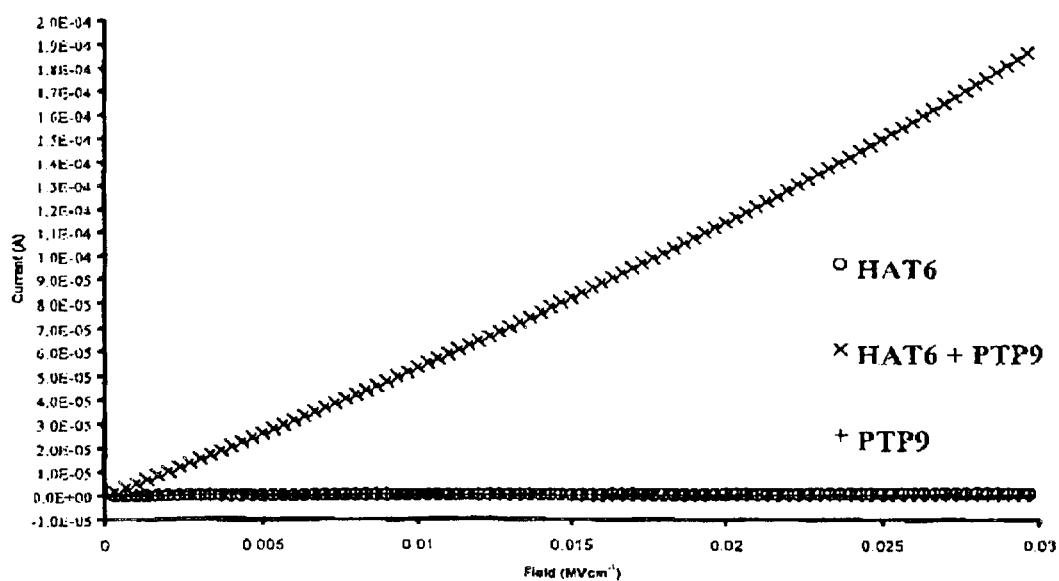
Figure 4: The IV characteristics of 2,3,6,7,10,11-hexakis-(4-nonylphenyl)-triphenylene, 2,3,6,7,10,11-hexahexyloxytriphenylene and their 1:1 mixture

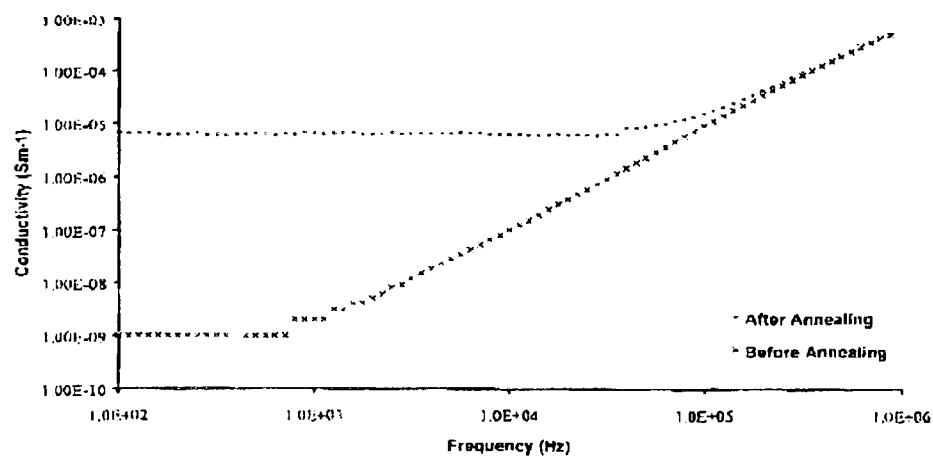
Figure 5: Frequency dependent conductivity before and after the mixture of 2,3,6,7,10,11-hexakis-(4-nonylphenyl)-triphenylene and 2,3,6,7,10,11-hexahexyloxytriphenylene is annealed

FAMILY OF CONDUCTING LIQUID CRYSTALS

RELATED APPLICATIONS

This application claims priority under 35 U.S.C. §371 from PCT/GB00/04691, (published under PCT Article 21(2) in English), filed on Dec. 8, 2000, which claims priority to Great Britain Application Serial No. 9928883.9, filed on Dec. 8, 1999, the disclosures of which are incorporated by reference herein in their entireties.

This invention relates to novel mixtures of compounds and, in particular, novel mixtures that exist as discotic liquid crystals and which have significantly improved liquid crystal and conductive properties. The invention also relates to certain novel compounds per se.

Several potential applications of discotic liquid crystals which are based on a combination of their processability and their ability to act as semiconductors have already been described. These include their use as (1) conducting interconnects in stacked silicon chip systems (2) as conducting layers in photoreproductive and electrophotographic systems (3) as active elements in electronic 'nose' arrays (4) as conductive elements in spatial light modulators and many others and as (5) electron/hole transporting materials in light emitting diodes.

Thus according to the main feature of the invention we provide a mixture comprising a molecule of formula I;

Formula I

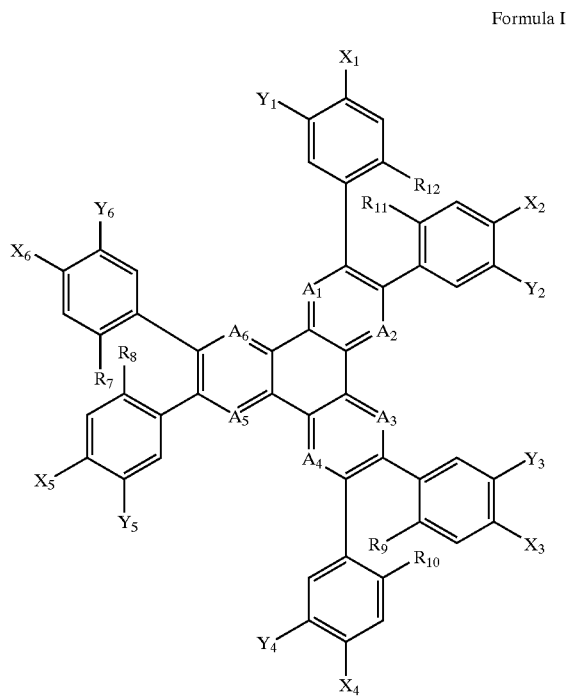

in which $A_1, A_2, A_3, A_4, A_5$ and $A_6$, which may be the same or different, are each N or —CH;

$Y_1, Y_2, Y_3, Y_4, Y_5$ and $Y_6$, which may be the same or different, are each hydrogen or $C_1$ to $C_{12}$ alkoxy;

$X_1, X_2, X_3, X_4, X_5$ and $X_6$, which may be the same or different, are each hydrogen, $C_1$ to $C_{12}$ alkoxy or alkyl $C_1$ to $C_{12}$; and $R_7, R_8, R_9, R_{10}, R_{11}$ and $R_{12}$ are each hydrogen, or each of $R_7$ and $R_8$, $R_9$ and $R_{10}$ and $R_{11}$, and $R_{12}$ may form a bond; and a molecule of formula II;

Formula II

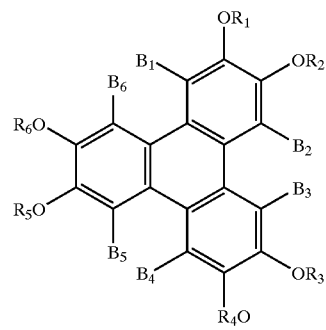

in which $R_1, R_2, R_3, R_4, R_5$ and $R_6$, which may be the same or different, are each alkyl or substituted (and/or chiral) alkyl $C_1$ to $C_{16}$, acyl $C_1$ to $C_{16}$, polyethyleneoxy, a flexible connection to a polymer backbone or part of a polymer backbone in homopolymers, copolymers or block copolymers; and $B_1, B_2, B_3, B_4, B_5$ and $B_6$ a, which may be the same or different, are each, hydrogen, alkyl $C_1$ to $C_{16}$, alkoxy $C_1$ to $C_{16}$, nitro, halogeno, cyano, amido, diazo or ester, e.g. alkyl $C_1$ to $C_{16}$ ester.

By the term "mixture" we mean a combination of compounds of formula I and formula II. In such combinations, quadrupolar attractions and van der Waals forces, between compounds of formula I and compounds of formula II suggests that the mixtures exist as compounds per se. Thus, any reference to mixtures of compounds of formula I and II should be construed accordingly.

In a preferred mixture of the invention, in the compound of formula I each of $A_1, A_2, A_3, A_4, A_5$ and $A_6$ are the same.

When each of $A_1, A_2, A_3, A_4, A_5$ and $A_6$ is N, then each of $Y_1, Y_2, Y_3, Y_4, Y_5$ and $Y_6$ preferentially represents hydrogen or alkoxy $C_3$ to $C_8$. Further, when each of $A_1, A_2, A_3, A_4, A_5$ and $A_6$ is N, then each of $X_1, X_2, X_3, X_4, X_5$ and $X_6$ is preferably $C_2$ to $C_{12}$ alkyl or $C_4$ to $C_{12}$ alkoxy, more preferably $C_6$ to $C_9$ alkyl or $C_6$ to $C_9$ alkoxy. Most preferably, when each of $A_1, A_2, A_3, A_4, A_5$ and $A_6$ is N, then each of $X_1, X_2, X_3, X_4, X_5$ and $X_6$ is either $C_9$ alkyl or $C_6$ alkoxy. We especially prefer each of $X_1, X_2, X_3, X_4, X_5$ and $X_6$ to be the same $C_9$ alkyl or each of $X_1, X_2, X_3, X_4, X_5$ and $X_6$ to be the same $C_6$ alkoxy.

When each of $A_1, A_2, A_3, A_4, A_5$ and $A_6$ is N, especially preferred mixtures are those in which each of $Y_1, Y_2, Y_3, Y_4, Y_5$ and $Y_6$ is hydrogen and each of $X_1, X_2, X_3, X_4, X_5$ and $X_6$ is $C_9$ alkyl, or, alternatively, each of $Y_1, Y_2, Y_3, Y_4, Y_5$ and $Y_6$ is $C_6$ alkoxy and each of $X_1, X_2, X_3, X_4, X_5$ and $X_6$ is $C_6$ alkoxy.

When each of $A_1, A_2, A_3, A_4, A_5$ and $A_6$ is C—H, then each of $Y_1, Y_2, Y_3, Y_4, Y_5$ and $Y_6$ preferentially represents hydrogen or alkoxy $C_3$ to $C_8$, preferably hydrogen or alkoxy $C_5$ to $C_7$ and most preferably hydrogen or alkoxy $C_6$.

When each of $A_1, A_2, A_3, A_4, A_5$ and $A_6$ is C—H, then each of $X_1, X_2, X_3, X_4, X_5$ and $X_6$ is $C_2$ to $C_{12}$ alkyl or $C_2$ to $C_{12}$ alkoxy. When each of $X_1, X_2, X_3, X_4, X_5$ and $X_6$ is alkoxy, they are preferably $C_6$ to $C_{12}$ alkoxy.

Preferred mixtures are those in which compounds of formula I are compounds of formula III;

Formula III

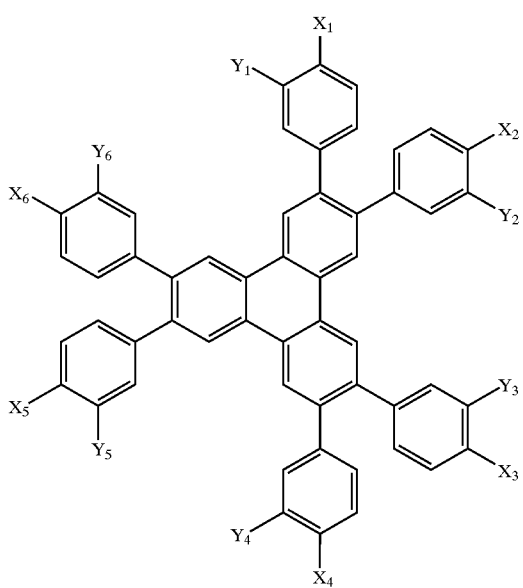

in which $X_1$, $X_2$, $X_3$, $X_4$, $X_5$ and $X_6$ are each the same and are selected from —$C_9H_{19}$, —$C_{12}H_{25}$, —$OC_6H_{13}$ and —$OC_{11}H_{23}$; and each of $Y_1$, $Y_2$, $Y_3$, $Y_4$, $Y_5$ and $Y_6$ are each the same and are selected from hydrogen and —$OC_6H_{13}$.

Further preferred mixtures are those in which the compounds of formula I are compounds of formula IV;

Formula IV

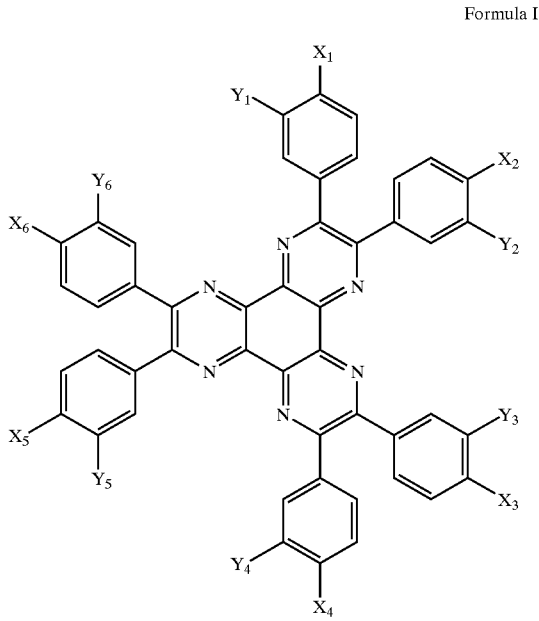

in which $X_1$, $X_2$, $X_3$, $X_4$, $X_5$ and $X_6$ are each the same and are selected from —$C_9H_{19}$, and —$OC_6H_{13}$; and
each of $Y_1$, $Y_2$, $Y_3$, $Y_4$, $Y_5$ and $Y_6$ are each the same and are selected from hydrogen and —$OC_6H_{13}$.

In a preferred mixture of the invention, in the molecule of formula II each of $R_1$, $R_2$, $R_3$, $R_4$, $R_5$ and $R_6$ are the same and $B_1$, $B_2$, $B_3$, $B_4$, $B_5$ and $B_6$ are hydrogen. Preferably, each of $R_1$, $R_2$, $R_3$, $R_4$, $R_5$ and $R_6$ are alkyl $C_3$ to $C_{16}$, more preferably alkyl $C_4$ to $C_{11}$ and most preferably $C_6$ or $C_{11}$ alkyl. The most preferred compounds of formula II are 2,3,6,7,10,11-hexahexyloxytriphenylene and 2,3,6,7,10,11-hexaundecyloxytriphenylene.

A further preferred mixture of the invention, contains the compound of formula II in which each of $R_1$, $R_2$, $R_3$, $R_4$, $R_5$ and $R_6$ are the same and are alkyl $C_3$–$C_{16}$, more preferably $C_4$–$C_{11}$ alkyl and most preferably $C_6$ alkyl. $B_1$, $B_2$, $B_3$, and $B_4$ are hydrogen and $B_5$ and $B_6$ are the same or different and are each or both hydrogen or fluorine. Most preferable is the compound formed by the mixture of formula I with formula II in which formula II is 1,4-difluoro-2,3,6,7,10,11-hexahexyloxytriphenylene. These mixtures are advantages in that the mesophase persists well below room temperature.

Liquid crystal phases can be induced in non-mesogenic materials such as those of formula II in which each of $R_1$, $R_2$, $R_3$, $R_4$, $R_5$ and $R_6$ are the same or different and are alkyl $C_2$–$C_{11}$ or ethyleneoxy $C_3$–$C_9$. More preferably when $R_1$, $R_2$, $R_3$, $R_4$, $R_5$ and $R_6$ are the same and ethyleneoxy $C_5$, and when $R_1$, $R_2$, $R_3$, $R_4$, $R_5$ and $R_6$ are a combination of ethyleneoxy $C_5$ and alkyl $C_6$. Most preferably when formula II is 2-(1,4,7-Trioxaoctyl)-3,6,7,10,11-pentahexyloxytriphenylene, 2,7-Di(1,4,7-trioxaoctyl)-3,6,10,11-tetrahexyloxytriphenylene, 2,7,10-Tri(1,4,7-trioxaoctyl)-3,6,11-trihexyloxytriphenylene or 2,3,6,7,10,11-Hexa(1,4,7-trioxaoctyl)triphenylene.

A preferred mixture contains a polythene main chain polymer with formula II as a side chain substituent in the form shown in formula V. X is alkyl $C_1$–$C_{10}$ or an ether oxygen linkage (—O—), and R is hydrogen or methyl. Addition of molecules of formula I to polymers such as those in Formula V produces a liquid crystal polymer which shows much better alignment properties than the polymer of formula V alone.

A further preferred mixture contains formula II as a functionality in polystyrene block copolymers of the form shown in formula VI. The ratio of n:m is from 6–18:1. The compound formed with formula I is again easier to align than the polymer of formula V alone with the added advantage that the blocks comprising the copolymer undergo micro-phase separation.

Formula V

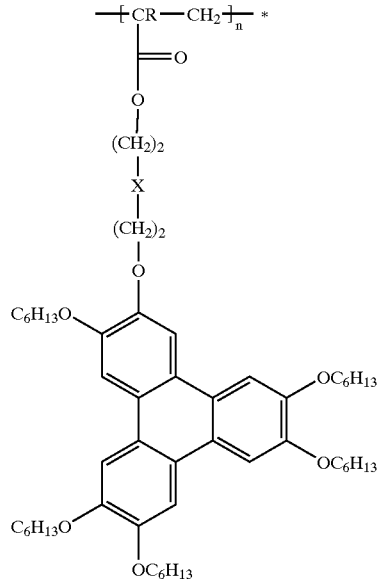

Formula VI

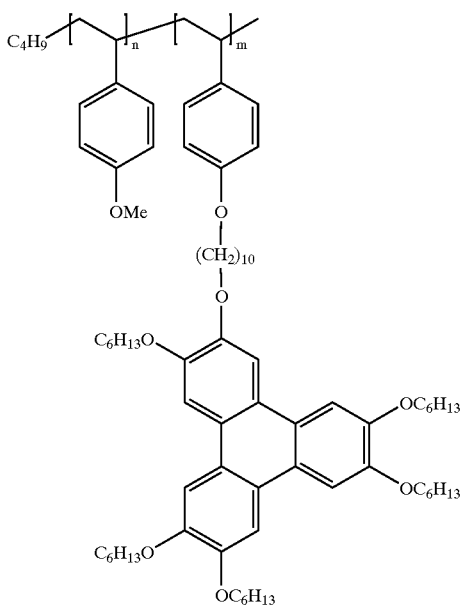

Another preferred mixture contains the formula I as a constituent part of the polymer backbone, the length of the flexible spacer n is between 6 and 18, most preferably 6, 12, and 18 and the number of molecules of formula II per polymer formula VII, m, is between 2 and 1000.

Formula VII

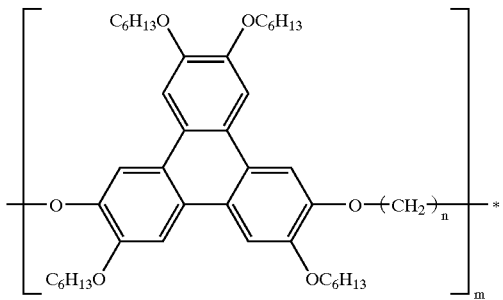

Block copolymers containing blocks of polyethylene oxide and blocks of formula VII can also be made to undergo micro-phase separation and further preferred mixtures contain the polymer of formula VIII. Where the number of molecules of formula I (m) is 10–100 and the number of ethyleneoxide groups in the side chains (n) is 200–500

In the mixture of the invention, specific compounds of formula I which may be mentioned include the following;
2,3,6,7,10,11-hexakis(4-n-nonylphenyl)dipyrazine[2,3-f:2', 3'-h]quinoxaline;
2,3,6,7,10,11-hexakis-(3,4-dehexyloxyphenyl)dipyrazino[2,3-f:2'3'-h]quinoxaline;
2,3,6,7,10,11-hexakis-4(-n-nonylphenyl)-triphenylene;
2,3,6,7,10,11-hexakis-(4-n-dodecylphenyl)triphenylene;
2,3,6,7,10,11-hexakis-(4-n-hexyloxy-phenyl)-triphenylene;
2,3,6,7,10,11-hexakis-(4-n-undecyloxy-phenyl)-triphenylene;
2,3,6,7,10,11-hexakis-(3,4-n-dihexyloxy-phenyl)-triphenylene; and
2,3,8,9,12,13,18,19,22,23,28,29-dodecakis(hexyloxy)hexabenz[a,c,k,m,v,w]trinaphthylene.

In the mixture of the invention, specific compounds of formula II which may be mentioned include the following;
2,3,6,7,10,11-hexahexyloxytriphenylene,
2,3,6,7,10,11-hexaundecyloxytriphenylene,
1,4-difluoro-2,3,6,7,10,11-hexahexyloxytriphenylene,
2-(1,4,7-trioxaoctyl)-3,6,7,10,11-pentahexyloxytriphenylene,
2,7-di(1,4,7-trioxaoctyl)-3,6,10,11-tetrahexyloxytriphenylene,
2,7,10-tri(1,4,7-trioxaoctyl)-3,6,11-trihexyloxytriphenylene,
2,3,6,7,10,11-hexa(1,4,7-trioxaoctyl)triphenylene,
acetic acid 2-hydroxy-3,6,7,10,11-pentahexyloxytriphenylene ester,
hexanoic acid 2-hydroxy-3,6,7,10,11-pentahexyloxytriphenylene ester,
4-biphenylcarboic acid 2-hydroxy-3,6,7,10,11-pentahexyloxytriphenylene ester,
4-nitrobenzoic acid 2-hydroxy-3,6,7,10,11-pentahexyloxytriphenylene ester,
3,5-dinitrobenzoic acid 2-hydroxy-3,6,7,10,11-pentahexyloxytriphenylene ester,
4-cyanobenzoic acid 2-hydroxy-3,6,7,10,11-pentahexyloxytriphenylene ester,
4-fluorobenzoic acid 2-hydroxy-3,6,7,10,11-pentahexyloxytriphenylene ester,
1-naphthoic acid 2-hydroxy-3,6,7,10,11-pentahexyloxytriphenylene ester,
2-naphthoic acid 2-hydroxy-3,6,7,10,11-pentahexyloxytriphenylene ester,
polythenes bearing formula II as a side chain substituent (formula V),
polyacrylates bearing formula II as a side chain substituent (formula VI
polymers containing formula II as part of the polymer backbone (formula VII),

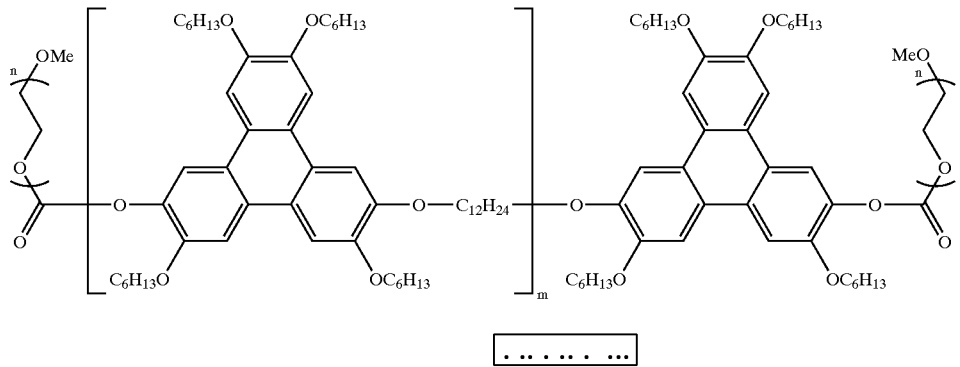

block copolymers containing a central core of polymer with formula II as part of the polymer backbone surrounded by blocks of poly(ethyleneoxide) with molecular weights in the range 750–2000 (formula VIII).

Thus the most preferred mixtures of the invention are mixtures comprising a compound of formula I selected from the group;

2,3,6,7,10,11-hexakis(4-nonylphenyl)dipyrazine[2,3-f:2',3'-h]quinoxaline;
2,3,6,7,10,11-hexakis-(4-nonylphenyl)-triphenylene;
2,3,6,7,10,11-hexakis-(4-dodecylphenyl)triphenylene;
2,3,6,7,10,11-hexakis-(4-hexyloxy-phenyl)-triphenylene;
2,3,6,7,10,11-hexakis-(4-n-undecyloxy-phenyl)-triphenylene;

and a compound of formula II selected from the group;

2,3,6,7,10,11-hexahexyloxytriphenylene,
2,3,6,7,10,11-hexaundecyloxytriphenylene,
1,4-difluoro-2,3,6,7,10,11-hexahexyloxytriphenylene,
2-(1,4,7-trioxaoctyl)-3,6,7,10,11-pentahexyloxytriphenylene,
2,7-di(1,4,7-trioxaoctyl)-3,6,10,11-tetrahexyloxytriphenylene,
2,7,10-tri(1,4,7-trioxaoctyl)-3,6,11-trihexyloxytriphenylene,
2,3,6,7,10,11-hexa(1,4,7-trioxaoctyl)triphenylene,
acetic acid 2-hydroxy-3,6,7,10,11-pentahexyloxytriphenylene ester,
hexanoic acid 2-hydroxy-3,6,7,10,11-pentahexyloxytriphenylene ester,
4-biphenylcarboic acid 2-hydroxy-3,6,7,10,11-pentahexyloxytriphenylene ester,
4-nitrobenzoic acid 2-hydroxy-3,6,7,10,11-pentahexyloxytriphenylene ester,
3,5-dinitrobenzoic acid 2-hydroxy-3,6,7,10,11-pentahexyloxytriphenylene ester,
4-cyanobenzoic acid 2-hydroxy-3,6,7,10,11-pentahexyloxytriphenylene ester,
4-fluorobenzoic acid 2-hydroxy-3,6,7,10,11-pentahexyloxytriphenylene ester,
1-naphthoic acid 2-hydroxy-3,6,7,10,11-pentahexyloxytriphenylene ester,
2-naphthoic acid 2-hydroxy-3,6,7,10,11-pentahexyloxytriphenylene ester,
1,4-difluoro-2,3,6,7,10,11-hexakis(hexyloxy)triphenylene, and
polythenes bearing formula II as a side chain substituent (formula V),
polyacrylates bearing formula II as a side chain substituent (formula VI
polymers containing formula II as part of the polymer backbone (formula VII),
block copolymers containing a central core of polymer with formula II as part of the polymer backbone surrounded by blocks of poly(ethyleneoxide) with molecular weights in the range 750–2000 (formula VIII).

The compounds of formula I are novel per se.

Thus, according to a further feature of the invention we provide a compound of formula I

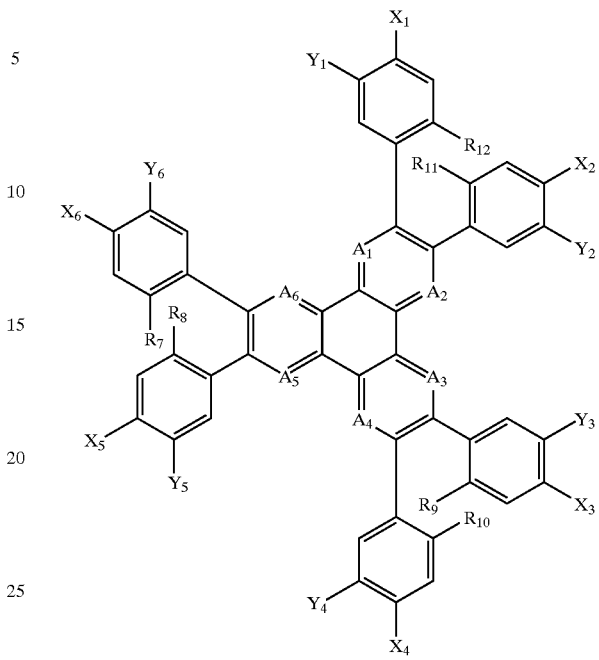

Formula I in which $A_{1-6}$, $X_{1-6}$, $Y_{1-6}$ and $R_{7-12}$ are as defined above; provided that the compound of formula I is not 2,3,6,7,10,11-hexakis(4-n-nonylphenyl)dipyrazine[2,3,-f:2,3-h]quinoxaline.

The compounds of formula I are especially advantageous in that they may be mixed with compounds of formula II to form novel compounds which possess properties as, inter alia, highly ordered and highly conducting liquid crystals.

Certain compounds of formula II are also novel per se.

Thus according to the invention we also provide a novel compound of formula II selected from the group;
1,4-difluoro-2,3,6,7,10,11-hexahexyloxytriphenylene,
2-(1,4,7-trioxaoctyl)-3,6,7,10,11-pentahexyloxytriphenylene,
2,7-di(1,4,7-trioxaoctyl)-3,6,10,11-tetrahexyloxytriphenylene,
2,7,10-tri(1,4,7-trioxaoctyl)-3,6,11-trihexyloxytriphenylene,
acetic acid 2-hydroxy-3,6,7,10,11-pentahexyloxytriphenylene ester,
hexanoic acid 2-hydroxy-3,6,7,10,11-pentahexyloxytriphenylene ester,
4-biphenylcarboic acid 2-hydroxy-3,6,7,10,11-pentahexyloxytriphenylene ester,
4-nitrobenzoic acid 2-hydroxy-3,6,7,10,11-pentahexyloxytriphenylene ester,
3,5-dinitrobenzoic acid 2-hydroxy-3,6,7,10,11-pentahexyloxytriphenylene ester,
4-cyanobenzoic acid 2-hydroxy-3,6,7,10,11-pentahexyloxytriphenylene ester,
4-fluorobenzoic acid 2-hydroxy-3,6,7,10,11-pentahexyloxytriphenylene ester,
1-naphthoic acid 2-hydroxy-3,6,7,10,11-pentahexyloxytriphenylene ester,
1,4-difluoro-2,3,6,7,10,11-hexakis(hexyloxy)triphenylene, and
block copolymers containing a central core of polymer with formula II as part of the polymer backbone surrounded by blocks of poly(ethyleneoxide) with molecular weights in the range 750–2000 (formula VIII).

According to the invention we also provide a process for the manufacture of a compound of formula I which comprises reacting a hexahalotriphenylene or a hexahaloquinoxaline with a boronic ester of formula V;

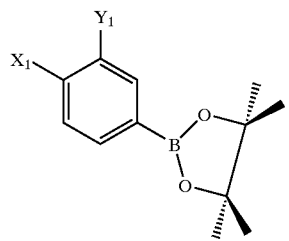

Synthesis of the quinoxalines involves a straightforward condensation of hexaaminobenzene with the appropriate benzil but to make the hexakis (4-alkoxyphenyl) triphenylenes a variation on the normal Suzuki reaction conditions had to be employed. The conditions required for this type of polyarylation are more demanding than those for simple aryl—aryl coupling. Under standard Suzuki coupling conditions (0.3 mol % Pd(0) as Pd(PPh$_3$)$_4$, toluene, water Na$_2$CO$_3$, reflux under argon for 24 hours) the reaction of the appropriate aryl boronic acid with hexabromotriphenylene gave the product formula III contaminated with a reduction product. Competitive reduction under these reaction conditions is a well-known problem. Ordinarily it is not significant since it often only amounts to only 1–2% and the by-product is usually easily removed. However, in this case the by-product is very difficult to remove and the "error is cumulative" giving 5–12% of the reduction product. To overcome this problem we have modified the Suzuki protocol to minimise reduction. A stronger base was used to improve the rate of metathesis of the boronic acid species and DME was used to give a homogenous reaction medium. In order to prevent excessive de-borylation of the boronic acid starting material, the less labile pinacol ester (above) was used. This ester is also easier to purify (by distillation or column chromatography) than the acid and is more stable with respect to temperature, pH and oxygen. These modifications improved the yield and purity of formula III giving a product in which the by-product could no longer be detected by $^1$H NMR.

The pioneering work of the group of Mullen suggested that oxidative cyclisation of compounds of formula I should yield systems with exceptionally large aromatic cores. This was achieved using dichloromethane/FeCl$_3$ followed by a reductive methanol work up and excellent yields were obtained (70%, 2 hrs at 25° C.). This is a new type of polynuclear aromatic core.

We also provide a method of manufacturing a mixture and or a liquid crystal as hereinbefore described which comprises mixing a compound of formula I with a compound of formula II.

2,3,6,7,10,11-hexahexyloxytriphenylene is known to display a hexagonal columnar mesophase between about 70 and 100° C. However the novel mixtures of the invention comprising a compound of formula II, e.g. 2,3,6,7,10,11-hexahexyloxytriphenylene, and a compound of formula I form a novel liquid crystal with a hexagonal columnar phase at a higher temperature than 2,3,6,7,10,11-hexahexyloxytriphenylene alone. Thus, for example, a mixture of 2,3,6,7,10,11-hexahexyloxytriphenylene and 2,3,6,7,10,11-hexakis(4-nonylphenyl)dipyrazine[2,3-f:2',3'-h]quinoxaline form a novel liquid crystal with a hexagonal columnar phase at a temperature of between 130 and 240° C.

The mesophase properties are altered by changing the properties of either formula I or formula II possible combinations of which were discussed earlier. The properties of a selection of the most preferable combinations of formula I and formula II are shown in Table 1.

Thus according to a further feature of the present invention we provide a liquid crystal with a hexagonal columnar phase between temperatures of less than room temperature and 280° C. The low temperature phase of many of the mixtures is glassy, allowing the columnar order of the mesophase to persist at low temperature without the introduction of crystalline defects.

The liquid crystal of the invention especially comprises a mixture of compounds of formula I and formula II as hereinbefore described.

In the mixtures and liquid crystals of the invention the ratio of the compound of formula I and formula II may vary. However, it is preferred that the ratio is substantially 50:50.

TABLE 1

| Formula II Name | Phase Behaviour + Formula IV ($X_{1-6} = C_9H_{19}$, $Y_{1-6} = H$) | Phase Behaviour + Formula III ($X_{1-6} = C_9H_{19}$, $Y_{1-6} = H$) |
| --- | --- | --- |
| 2,3,6,7,10,11-hexahexyloxytriphenylene | K <0 Col$_h$ 240 (33) I | K <0 Col$_h$ 155 (19) I |
| 1,4-difluoro-2,3,6,7,10,11-hexakis(hexyloxy)triphenylene. | K <0 Col$_h$ 225.6 (36) I | K <0 Col$_h$ 129.3 (16) I |
| 2-(1,4,7-Trioxaoctyl)-3,6,7,10,11-pentahexyloxytriphenylene | Col 240.4 (28.7 J/g) I | Col 137 (15.2 J/g) I |
| 2,7-Di(1,4,7-trioxaoctyl)-3,6,10,11-tetrahexyloxytriphenylene | Col 231.8 (29.7 J/g) I | Col 117.7 (9.1 J/g) I |
| 2,7,10-Tri(1,4,7-trioxaoctyl)-3,6,11-trihexyloxytriphenylene | Col 226.3 (29.6 J/g) I | Col 88.0 (3.8 J/g) I |
| 2,3,6,7,10,11-Hexa(1,4,7-trioxaoctyl)triphenylene | Col 200.2 (19.9 J/g) I | Col 51.7 (17.4 J/g) I |
| 2-hydroxy-3,6,7,10,11-pentahexyloxytriphenylene esters of: | | |
| Acetic acid | K <0 Col$_h$ 214 (29.5) I | K <0 Col$_h$ 155 (15.4) I |
| Hexanoic acid | K <0 Col$_h$ 218 (31.1) I | K <0 Col$_h$ 166 (18.7) I |
| 4-Biphenylcarboic acid | K <0 Col$_h$ 228 (29.4) I | K <0 Col$_h$ 169 (17.0) I |
| 4-Nitrobenzoic acid | K <0 Col$_h$ 237 (29.9) I | K <0 Col$_h$ 180 (17.9) I |
| 3,5-Dinitrobenzoic acid | K <0 Col$_r$ 229 (28.2) I | K <0 Col$_{r1}$ 114.5 (0.5) Col$_{r2}$ 169 (13.0) I |

TABLE 1-continued

| Formula II Name | Phase Behaviour + Formula IV ($X_{1-6} = C_9H_{19}$, $Y_{1-6} = H$) | Phase Behaviour + Formula III ($X_{1-6} = C_9H_{19}$, $Y_{1-6} = H$) |
|---|---|---|
| 4-Cyanobenzoic acid | K <0 $Col_h$ 227 (27.2) I | K <0 $Col_h$ 175 (17.6) I |
| 4-Fluorobenzoic acid | K <0 $Col_h$ 231 (30.0) I | K <0 $Col_h$ 174 (19.6) I |
| 1-Naphthoic acid | K <0 $Col_h$ 205 (18.3) I | K <0 $Col_h$ 151 (10.9) I |
| 2-Naphthoic acid and Polymers | K <0 $Col_h$ 230 (32.8) I | K <0 $Col_h$ 176 (19.2) I |
| Formula V (X=O, R=H) | Col 235 (26.1) I | Col 147 (12.5) I |
| Formula VI (m:n = 6:1) | Glass 104 Col 228.8 (12.2) I | Glass 104 Col 127.1 (3.66) I |
| Formula VI (m:n = 18:1) | Col 243.1 (12.2) I | Cr 101 (0.1) Col 136.9 (−4.4) I |
| Formula VII (n = 8) | $Col_h$ 190.9 (2.4) I | Cr 48.7 (3.1), $Col_h$ 100.0 (2.4)1 |
| Formula VII (n = 12) | Cr 67.0 (1.0) $Col_h$ 194.8 (14.8) I | Glass 57.2 $Col_h$ 128.4 (9.2) I |
| Formula VII (n = 16) | Glass 90 $Col_h$ 245.3 (26.6) I | $Col_h$ 155.7 (2.5) I |
| Formula VIII (n = 20) | $Col_h$ 213.9 (15.1) I | Col 137.5 (8.85) I |
| Formula VIII (n = 40) | Cr 52 (15.2) $Col_h$ 223 (15.7) I | Cr 46.1 (11.29) Col 141.0 (6.6) I |

The unit cell parameters for the some of these mixtures are given in Table II.

| Molecule | $a_{hex}$ | $c_{hex}$ | cell density $g\text{Å}^{-2}$ | Number of reflections |
|---|---|---|---|---|
| 2,3,6,7,10,11-hexahexyloxytriphenylene | 24.2 | 3.55 | 0.671 | 3 |
| 2,3,6,7,10,11-hexakis(4-n-nonylphenyl)-dipyrazine[2,3-f:2',3'-h]quinoxaline | 30.5 | 3.55 | 0.728 | 7 |
| 2,3,6,7,10,11-hexakis-(4-nonylphenyl)-triphenylene | 29.6 | 3.55 | 0.769 | 7 |
| 2,3,6,7,10,11-hexahexyloxytriphenylene + 2,3,6,7,10,11-hexakis(4-n-nonylphenyl)-dipyrazine[2,3-f:2',3'-h]quinoxaline | 28.3 | 6.92 | 0.682 | 11 |
| 2,3,6,7,10,11-hexahexyloxytriphenylene + 2,3,6,7,10,11-hexakis-(4-nonylphenyl)-triphenylene | 27.0 | 7.07 | 0.732 | 15 |

The fact that there is a single column/column repeat distance and a hexagonal lattice shows that there cannot be segregated stacks of compounds of formula I and formula II. Thus there is an alternating stack structure in which a compound of formula I is stacked on a compound of formula II and so on.

Thus according to a further feature of the invention we provide a liquid crystal as hereinbefore described which has an alternating stack structure. We especially provide a liquid crystal which comprises an alternating stack of compounds of formula I and formula II.

In relation to the entries displayed in Table I it is important to note that:
1) There is 1:1 compound formation in the mixture of compounds of formula I and formula II. That the temperature of the clearing temperature of the 1:1 compound is generally above that of the individual components and that this 1:1 compound undergoes isothermal phase transitions. A specific example is given in FIG. 1 (the phase/composition diagram of HAT6 (2,3,6,7,10,11-hexahexyloxytriphenylene)+PDQ9 (2,3,6,7,10,11-hexakis(4-n-nonylphenyl)dipyrazine[2,3-f.2',3'-h]quinoxaline)
2) There may be induction of liquid crystalline behaviour. The 1:1 compounds give columnar liquid crystal phases whereas the individual components of formula I and formula II may either be mesogenic or non-mesogenic. Preferable examples are 2,3,6,7,10,11-Hexa(1,4,7-trioxaoctyl)triphenylene and 2-Naphthoic acid 2-hydroxy-3,6,7,10,11-pentahexyloxytriphenylene ester.
3) In the use of polymer derivatives of formula II 1:1 compounds with formula I are often easier to align by surface or shear interactions than the polymers on their own. Hence FIG. 2 shows the alignment of the mixture of Formula VII (n=12) with (2,3,6,7,10,11-hexakis(4-n-nonylphenyl)dipyrazine[2,3-f:2',3'-h]quinoxaline) compared to that of the polymer alone.
4) In the case of block copolymers of compound formula VIII, addition of the compound of formula I can induce microphase separation, for example when Formula VIII (n=40) is mixed with 2,3,6,7,10,11-hexakis(4-n-nonylphenyl)dipyrazine[2,3-f:2',3'-h]quinoxaline.
5) These new mixtures show enhanced conductive behaviour. Studies on the photoconductivity of 2,3,6,7,10,11-hexahexyloxytriphenylene have found that there exist clear hole transits in the mesophase while the transient photocurrent displayed a featureless decay in the crystalline phase. Holes in the mesophase of that material were found to have a mobility of $\mu_\pi = 3.0 \times 10^{-4}$ $cm^2 V^{-1} s^{-1}$, which is generally a 200 fold enhancement over known liquid crystals. Detailed analysis of the featureless photocurrent transient decays demonstrated that the columnar stacks behave like one dimensional semiconductors and that the holes had a range of S=4 μm before deep trapping in the crystalline phase. Thus discotics have already been demonstrated as hole transporting layers. The liquid crystals of the invention demonstrate improved hole mobility and hole range by using a mixture designed to give favourable π-stacking. Thus the liquid crystals of the invention have an enhanced conductivity over known liquid crystals, with an enhancement factor of from 10 to $10^5$ For sandwich samples of thickness 25 μm, of 2,3,6,7,10,11-hexaundecyloxytriphenylene (HAT11) the photocurrent is not detectable in either the discotic or crystalline phase. This places an upper limit on the peak photocurrent, $I_p$ of $I_p<<4\times10^{-7}$ A even at the highest applied electric fields of $E=6.0MVm^{-1}$. This is in stark contrast to the photoconductivity of 2,3,6,7,10,11-hexahexyloxytriphenylene where the magnitude of the peak photocurrent in the discotic phase at similar electric field and sample thickness was $I_p=10^{-5}$ A.

With 1:1 mixture of 2,3,6,7,10,11-hexaundecyloxytriphenylene and 2,3,6,7,10,11-hexakis-(4-nonylphenyl)-triphenylene however, there is a transient photocurrent generated by a thin sheet of positive carriers of thickness, δ—0.1 μm travelling from a top electrode, where they are generated by a laser pulse, to a bottom counter electrode under the influence of an electric field (FIG. 3).

Taking a mobility of 0.017 $cm^2V^{-1}s^{-1}$, as representative of the discotic phase, it is noteworthy that in the system of the invention the mobility has increased, by a factor ≈57, in comparison to that previously found for HAT11. Also of interest is the observation in the mixture of a clear transit even in the low temperature regime. From the pre transit time photocurrent decay it is possible to estimate a trapping time and a consequent carrier schubweg and the increased mobility are indicative of a great improvement in the ordering of the columnar stacks in the mixed system. This ordering is a direct consequence of the mixture as 2,3,6,7,10,11-hexakis-(4-nonylphenyl)-triphenylene alone does not photoconduct. Ordering has been found elsewhere to lead to higher mobility in compounds forming a helical columnar phase and to dominate the mobility parallel to the column in hexagonal phases. Therefore, according to a yet further feature of the invention we provide a liquid crystal which has enhance hole electron mobility and charge carrier schubweg.

Conductivity in these systems has also been investigated by sandwiching a homeotropic film of the mixtures between conducting ITO coated glass electrodes. FIG. 4 shows the IV characteristics of 2,3,6,7,10,11-hexakis-(4-nonylphenyl)-triphenylene, 2,3,6,7,10,11-hexahexyloxytriphenylene and their 1:1 mixture FIG. 5 shows the frequency dependent AC conduction properties of the mixture before and after the sample cell is annealed by the action of heat and applied field. Typically the annealing process is carried out in the liquid crystalline phase of the mixture, a field is then applied, the intensity of which is steadily increased until the resistance of the sample begins to suddenly fall (typically 20V across a 6 μm cell).

We also provide the use of a mixture of a compound of formula I and a compound of formula II in the manufacture of a liquid crystal as hereinbefore described.

We further provide the use of a compound of formula I in the manufacture of a mixture or a liquid crystal as hereinbefore described.

We yet further provide the use of a compound of formula II in the manufacture of a mixture or a liquid crystal as hereinbefore described.

The invention will now be described by way of example only.

EXAMPLE 1

Photoconduction Studies

Electrode cells were fabricated by evaporating aluminium on two quartz slides making one of them semitransparent. The two slides are placed on top of one another being separated by 25 μm Teflon spacers. The slides were held in an assembly allowing temperature control. By melting the compound at the entrance to the cell it fills the cell by capillary flow. The thickness of the cell and its uniformity was monitored using interference fringes and measurement of the interference transmission spectrum using a Hitachi U3000 spectrophotometer.

The potential was supplied by a Fluke high voltage power supply. A lambda Physik EMG101 nitrogen laser at 337 nm with a 6 ns pulse width was used to excite the photocurrent transients. The light intensity was controlled using neutral density filters and kept low to avoid distortion of the resulting signal by space charge. The photocurrents were detected as a voltage across a 50 Ω input resistor to a high speed 592 differential video pre amplifier with ×100 gain. The two outputs of the 592 act as input to EL2002 50 Ω line drivers in turn delivering the signal to a 50 Ω terminated Tektronix digitising oscilloscope, TDS 320. The laser emits radio frequency interference, RFI, picked up by the detection apparatus so it is necessary to collect a second baseline signal with no light on the sample. In this way, in post acquisition processing the RFI was subtracted and the signal greatly cleaned up. White noise was also reduced by signal averaging.

EXAMPLE 2

Synthesis

Compound Preparation.

The mixtures/compounds were prepared by dissolving the components, in a 1:1 molar ratio, in dichloromethane. The components were weighed to within a tolerance of ±0.001 g. To aid dissolution of the components the solution was warmed gently in an ultra-sonic bath. Rotary evaporation under reduced pressure was used to remove the solvent, leaving a thin film of the compound on the walls of the flask. This thin film was dried at 40° C. under vacuum (0.01 mmHg) for 5 days. The compound was then scraped from the flask and powdered.

Thermal Characterisation.

The thermal behaviour of all the materials was investigated by polarising optical microscopy (Olympus BH-2 microscope and with a Linkam hot stage) and differential scanning calorimetry (Perkin-Elmer DSC 7, 2–3 mg in closed Al pans) with heating and cooling scans performed at 10° C.min$^{-1}$. Onset values (° C.) are reported together with the associated transition enthalpies (ΔH) in kcal mol$^{-1}$. Exothermic transitions are conventionally reported with a negative enthalpy change.

The phase-composition diagrams were constructed using OPM and DSC data collected for mixtures with varying amounts of each component. For mixtures containing >10% of both components the sample was prepared by weighing the components accurately as described in Section 0. For mixtures where one component was present as less than 10% of the total, accurately prepared, standard solutions of the components prepared and these were mixed in the correct proportions using a pipette.

X-ray Diffraction Experiments.

X-ray diffraction experiments were performed at room temperature (in the crystalline phase) and, for those compounds with mesomorphic properties, at a range of temperatures increasing towards the upper limit of the columnar phase(s). The diffraction pattern was collected on film using a pinhole camera consisting of a Philips generator and tubes, nickel filtered Cu $K_\alpha$ radiation of wavelength $\lambda$=0.154 nm, and a Lindemann sample tube (1.5 mm inner diameter) to plate distance of 135.5 mm.

Powder samples were packed into the capillary, which was degassed with argon before the end was cleaned (dichloromethane), dried and sealed using a flame. Sticky or fine powders were initially loaded by forming a plug of material in the mouth of the capillary tube. The end of the tube was cleaned with dichloromethane (to avoid contamination with charred organic material) and dried before being sealed. Once the tube was sealed it was placed into a pre-heated aluminium holder and centrifuged for five minutes or until the plug of material was packed into the bottom of the tube and no air bubbles could be seen.

Exposure times in excess of three hours were required to get good resolution of both wide and small angle regions. The film was developed for five minutes, fixed for five minutes and then washed for one hour before being hung to dry at room temperature overnight. The diameters of the diffraction rings were measured using a ruler with the aid of a light box. A spreadsheet was used to collate the data for each sample and temperature and calculate the lattice distances (to within ±0.3 Å). A small in-house package was used to assist in the assignment of the unit cell parameters.
NMR Experiments.

$^1H$ and $^{13}C$ NMR ($^1H$ {BB} and INEPT) spectra were acquired on a 400 MHz Bruker AM400 NMR spectrometer; chemical shifts are reported in $\delta$ units (ppm, relative to $Me_4Si$ (TMS)). COSY and HMQC NMR experiments were run as necessary, to assign any ambiguous peaks in the $^1H$ or $^{13}C$ spectra. $^1H$ {BB} refers to broadband decoupling of protons. $^{11}B$ spectra were also proton decoupled. In the spectra of boronic acids and esters it is worth noting that the resonance due to the carbon atom attached directly to boron is so broad that its detection is impossible (quantum effect).
Mass Spectra Mass spectra were recorded on a VG Autospec instrument and all peaks >20% were routinely recorded unless stated; FAB+ refers to the caesium atom bombardment method of ionisation. Unless stated the electron ionisation method was used.
Spectroscopic Measurements UV/VIS (250–600 nm, 1 cm path length quartz cell) were recorded on a Perkin-Elmer Lambda series 2 spectrometer, the extinction coefficients ($\epsilon$) are given in units of $dm^3mol^{-1}cm^{-1}$. FTIR spectra were recorded on a Perkin-Elmer 1760X FTIR spectrometer in the range 4000–600 $cm^{-1}$ as a liquid film or Nujol mull between polished NaCl disks.

EXAMPLE 3
General Synthesis of Boronic Esters

Chemicals and solvents (AR) grade were obtained from Sigma-Aldrich and, unless mentioned, were used without further purification. Column chromatographic separations were performed on silica gel (Merck, Kieselgel 9385 Type 60). Thin layer chromatography (TLC) was performed on aluminium sheets pre-coated with silica gel (Whatman AL SIL G/UV plates). Petroleum ether refers to the petroleum fraction boiling 40–60° C., which was double distilled before use.

The boronic acid, synthesised by literature methods known per se, (1 mmol) was weighed into a clean, dry round bottom flask fitted with a reflux condenser and a gas bubbler. Pinacol (distilled, 1.1 mol) was added in 5 ml of dry, distilled tetrahydrofuran. The reaction mixture was refluxed under nitrogen for at least one hour. Removal of the solvent yields the crude product, which was purified by flash column chromatography (1:1 dichloromethane/petroleum ether as eluent).

EXAMPLE 4
General Synthesis of Hexakis(4-alkoxy phenyl) triphenylenes 2,3,6,7,10,11-hexahexyloxytriphenylene (1 mmol) was added to a mixture of dimethyl ether (DME) (50 ml) and water (2 ml). Argon was bubbled through the suspension for fifteen minutes before adding tetrakis-triphenylphosphine palladium (0) (0.3–3 mol % Pd per reaction site). The boronic ester (7 mmol) was added carefully under a stream of argon and stirring was continued for 10 minutes. Finally barium hydroxide monohydrate (7 mmol) was added. The mixture was heated to 80° C. and stirred under argon until the reaction was complete (1–3 days). cool water was added to the reaction mixture and the organic phase extracted with ether. The combined extracts were washed with water and dried over magnesium sulphate. The dry organic phase was passed through a short silica column and the solvent removed to give the crude product as a straw coloured oil. Flash column chromatography was used to purify the product and (where possible) it was precipitated from ether (–30° C. for 14 days) or ethanol.

The following compounds were synthesised using the general methods set out above;

EXAMPLE 5
2,3,6,7,10,11-Hexakis-(4-n-nonylphenyl)-triphenylene (PTP9)

Yield 88%. White solid M.p.53° C. and 65° C. Found: C, 89.9; H, 10.2. $C_{108}H_{144}$ requires C, 89.9; H, 10.1%); IR(Nujol) $v\sim$=1909 $cm^{-1}$ (C=C); $^1H$ NMR (300 MHz, $CDCl_3$, 25° C., TMS): $\delta$=0.81 (t, $^3J(H,H)$=7 Hz, 18H; 6×—$CH_3$), 1.20 (m, 72H; 6×—$(CH_2)_6$—), 1.55 (m, 12H; 6×—$CH_2CH_2$—Ar), 2.53 (t, $^3J(H,H)$=7 Hz, 12H; 6×$CH_2CH_2$—Ar), 7.02 (d, $^3J(H,H)$=8.0 Hz, 12H; 6×2—$CH$_, Phenyl $C_{3,6}$), 7.15 (d, $^3J(H,H)$=8.0 Hz, 12H; 6×22—$CH^-$, Phenyl $C_{3,6}$), 7.15 (d, $^3J(H,H)$=8.0 Hz, 12H; 6×2—CH—, Phenyl $C_{2,5}$), 8.61 (s, 6H; 6—CH—, triphenylene): $^{13}C$ NMR (75 MHz, $^1H$\{BB\} and DEPT, $CDCl_3$, 25° C., TMS): $\delta$=14.53 ($CH_3$), 23.10 ($CH_2$), 29.73 ($CH_2$), 29.73 ($CH_2$), 29.76 ($CH_2$), 29.76 ($CH_2$), 29.96 ($CH_2$), 30.02 ($CH_2$), 31.82 ($CH_2$), 32.33 ($CH_2$), 36.04 ($CH_2$), 125.85 (C, triphenylene $C_{1,4,5,8,9,12}$), 128.40 (CH, Phenyl $C_{2,6}$), 129.22 (C, triphenylene $C_{4a,4b,8a,8b,12a,12b}$), 130.34 9CH, Phenyl $C_{3,5}$), 139.27 (C, Phenyl $C_4$), 140.24 (C, Phenyl $C_1$), 141.76 (C, triphenylene $C_{2,3,6,7,10,11}$); MS (FAB+): m/z(%): 1442 (100) [$M^+$], 1370(10), 1329(15), 1239(35).

EXAMPLE 6
2,3,6,7,10,11-Hexakis-(4-n-dodecylphenyl)-triphenylene (PTP12)

Yield 78%. White solid M.p. 36° C. Found: C, 89.1; H, 10.5. $C_{126}H_{180}$ requires C, 89.3; H, 10.5%); IR(Nujol): $v\sim$=1909 $cm^1$(C=C); 1H NMR (300 MHz, $CDCl_3$, 25° C., TMS): $\delta$=0.91 (t, $^3J(H,H)$=7 HZ, 18H; 6×—$CH_3$), 1.30 (m, 84H; 6×—$(CH_2)_7$—), 1.33 (m. 12H; 6×—$CH_2CH_2CH_2CH_2$—Ar), 1.34 (m, 12H; 6×$CH_2CH_2CH_2$—Ar), 1.65 (m, 12H; 6×—$CH_2CH_2$—Ar), 2.63 (t, $^3J(H,H)$-7 Hz, 12H; 6×$CH_2CH_2$—Ar), 7.12 (d $^3J(H,H)$=8.2 Hz, 12H; 6×2—CH—, phenyl $C_{3,5}$), 7.27 (d, $^3J(H,H)$=8.2 Hz, 12H; 6×2—CH—, phenyl $C_{2,6}$), 8.71 (s, 6H; 6×—CH—, triphenylene; $^{13}C$ NMR (75 MHz, $^1H$\{BB\} and DEPT, $CDCl_3$, 25°, TMS): $\delta$=14.53 ($CH_3$), 23.11 ($CH_2$), 29.75 ($CH_2$), 29.79 ($CH_2$), 29.97 ($CH_2$), 30.08 ($CH_2$), 30.12 (2×$CH_2$), 30.81 (2×$CH_2$), 32.34($CH_2$), 36.04 ($CH_2$), 125.87 (CH, triphenylene $C_{1,4,5,8,9,12}$), 128.38 (CH, phenyl $C_{2,6}$), 129.22 (C, triphenylene $C_{4a,4,8a,8b,12a,12b}$), 130.35 (CH, phenyl $C_{3,5}$), 139.28 (C, phenyl $C_4$), 140.25 (C, phenyl $C_1$), 1421.74 (C, triphenylene $C_{2,3,6,7,10,11}$); MS (FAB+): m/z (%): 1694(75) [M+], 1552(10), 57(100).

EXAMPLE 7
2,3,6,7,10,11-Hexakis-(4-n-hexyloxy-phenyl)-triphenylene (PTPO6)

Yield 66%. White Solid M.p. 59° C. and 139° C. Found: C, 83.8; H, 8.65, $C_{90}H_{108}O_6$ requires C, 84.0; H, 8.5; O, 7.5%); IR (Nujol): v~=1908 cm$^{-1}$ (C=C); 1H NMR (300 MHz, $CDCl_3$, 25° C., TMS): δ=0.85 (t, $^3J(H,H)$=7 Hz, 18H; 6×$CH_3$), 1.28 (m, 24H; 6×—$(CH_2)_2$—), 1.40 (m, 12H; 6×$CH_2CH_2CH_2$—OAr), 1.72 (quint, $^3J(H,H)$=7 Hz, 12H; 6×$CH_2CH_2CH_2$—OAr), 3.89 (t, $^3J(H,H)$=7 Hz, 12H; 6×$CH_2CH_2$—OAr), 6.76 (d, $^3J(H,H)$=8.8 Hz, 12H; 6×2—CH—, phenyl $C_{3,5}$), 7.16 (d, $^3J(H<H)$=8.8 Hz, 12H; 6×2—CH—, phenyl $C_{2,6}$), 8.56 (s, 6H; 6×CH—, triphenylene); $^{13}C$ NMR (75 MHz, $^1H${BB} and DEPT, $CDCl_3$, 25° C., TMS): δ=14.46 ($CH_3$), 23.02 ($CH_2$), 26.16 ($CH_2$), 29.68 ($CH_2$), 30.98 ($CH_2$), 32.02 ($CH_2$), 68.39 ($CH_2$), 114.48 (CH, phenyl $C_{3,5}$), 125.73 (CH, triphenylene $C_{1,4,5,8,9,12}$), 129.08 (C, triphenylene $C_{4a,4b,8a,8b,12a,12b}$), 131.51 (CH, phenyl $C_{2,6}$), 134,29 (C, phenyl $C_1$), 139.81 (C, triphenylene $C_{2,3,6,7,10,11}$), 159.46 (C, phenyl $C_4$); MS (FAB+): m/z(5); 1285 (28) [M+], 1108(10), 109(25), 69(100).

EXAMPLE 8
2,3,6,7,10,11-Hexakis-(4-n-undecyloxy-phenyl)-triphenylene (PTPO11)

Yield 77%. Pale Yellow solid M.p. 66° C. Found C, 84.8; H, 10.2. $C_{120}H_{168}O_6$ requires C, 84.5; H, 9.9; O, 5.6%; IR(Nujol): v~=2300 cm$^{-1}$ (C=C), $^1H$ NMR (300 MHz, $DCDl_3$, 25° C., TMS: δ=0.92 (t, $^3J(H,H)$=7 Hz, 18H; 6×$CH_3$), 1.31 (m, 84H: 6×—$(CH_2)_r$), 1.60 (m, 12H; 6×$CH_2CH_2CH_2$—OAr), 1.82 (quint, $^3J(H,H)$=7 Hz, 12H; 6×—$CH_2CH_2CH_2$—OAr), 3.99 (t, $^3J(H,H)$=7 Hz, 12H; 6×$CH_2CH_2$—OAr), 6.90 (d, $^3J(H,H)$=8.5 Hz, 12H: 6×2—CH—, phenyl $C_{3,5}$), 7.28 (d, $^3J(H,H)$=8.5 Hz, 12H; 6×2—CH—, phenyl $C_{2,6}$), 8.66 (s, 6H, 6×—CH—, triphenylene); $^{13}C$ NMR (75 MHz, $^1H${BB} and DEPT, $CDCl_3$, 25° C., TMS): δ=14.54 ($CH_3$), 23.11 ($CH_2$), 26.50 ($CH_2$), 29.76 ($CH_2$), 29.77 ($CH_2$), 29.86 ($CH_2$), 29.86 ($CH_2$), 29.87 ($CH_2$), 30.03 ($CH_2$), 30.04 ($CH_2$), 32.33 ($CH_2$), 68.39 ($CH_2$), 114.48 (CH, phenyl $C_{3,5}$), 125.74 (CH, triphenylene $C_{1,4,5,8,9,12}$), 129.09 (C, triphenylene $C_{4a,4b,8a,8b,12a,12b}$), 131.52 (CH, phenyl $C_{2,6}$), 134.29 (C, phenyl $C_1$), 139.82 (C, triphenylene $C_{2,3,6,7,10,11}$) 158.47 (C, phenyl $C_4$); MS (FAB+): m/z(%): 1705(70) [M+], 1459(100), 1305(35), 79(30), 502(35), 423(40).

EXAMPLE 9
2,3,6,7,10,11-Hexakis(3,4-n-dihexyloxy-phenyl)-triphenylene (PTPO6$_2$)

Yield 40%. K: 65° C., $Col_1$: 135,1:. Found: C, 80.2; H, 9,5. $C_{126}H_{180}O_{12}$ requires C, 80.2; H, 9.6; O, 10.8%); IR(Nujol): c~=2350 cm$^{-1}$ (C=C); $^1H$ NMR (300 MHz, $CDCl_3$, 25° C., TMS): δ=0.84, (t, $^3J(H,H)$=7 Hz, 18H; 6×—$CH_3$), 0.84 (T, $^3j(h,h)$=7 Hz, 18H; 6×—$CH_3$), 1.27 (M, 24h; 6×—$(CH_2)_2$—), 1.42 (m, 24H; 6×2—$CH_2CH_2CH_2$—OAr), 1.74 (m, 12H; 6×—$CH_2CH_2CH_2$—OAr), 1.78 (m, 12H; 6×2$CH_2CH_2CH_2$—OAr), 3.95 (t, $^3J(H<H)$=7 Hz, 12H; 6×$CH_2,CH_2$—OAr), 3.98 (t, $^3J(H,H)$=7 Hz, 12H; 6×$CH_2CH2$—OAr), 6.86 (d, $^3J(H,H)$=9.0 Hz, 6H; 6×—CH—, phenyl $C_5$), 6.98 (dd, $^3J(H,H)$=9.0 Hz, $^4J(H,H)$=2 Hz, 6H; 6×—CH—, phenyl $C_6$), 7.00 (d, $^4J(H,H)$=2 Hz, 6H; 6×—CH—, phenyl $C_2$), 8.60 (s, 6H; 6×—CH—, triphenylene); $^{13}C$ NMR (75 MHz, $^1H${BB} and DEPT, $CDCl_3$, 25° C., TMS): δ=14.43 ($CH_3$), 23.03 ($CH_2$), 26.13 ($CH_2$), 29.72 ($CH_2$), 32.02 ($CH_2$), 69.93 ($CH_2$), 113.58 (CH, phenyl $C_2$), 114.59 (CH, phenyl $C_5$), 119.70 (CH, phenyl $C_6$,), 125.10 (CH, triphenylene $C_{1,4,5,8,9,12}$), 129.13 (C, triphenylene $C_{4a,4b,8a,8b,12a,12b}$), 134.76 (C, phenyl $C_1$), 148.87 (CH, phenyl $C_4$), 149.67 (C, phenyl $C_3$), 162 (C, triphenylene $C_{2,3,6,7,10,11}$); MS 9FAB+): m/z(%): 1894(10) [M+}, 554(100), 470(10), 310(50), 218(25).

EXAMPLE 10
2,3,8,9,12,13,18,19,22,23,28,29-dodecakis(hexyloxy) hexabenz[a,c,k,m,v,w]trinaphthylene 2,3,6,7,10,11-Hexakis(3,4-n-dihexyloxy-phenyl)-triphenylene (0.1 g, 5.3×10$^{-5}$ mol) was stirred in dry, distilled dichloromethane (10 ml). Iron (III) chloride (anhydrous, 0.22 g, 8.3×10$^{-4}$ mol) was then added carefully. A stream of nitrogen through the reaction mixture helps to remove the hydrogen chloride produced (which can act as a de-alkylating agent). After four hours methanol (HPLC, 5 m) was added, followed by dichloromethane (10 ml) and water (5 ml). The aqueous layer was extracted with dichloromethane (2×5 ml) and the combined organic extracts were washed with water (4×5 ml). Drying and removal of the solvent left 4 as a dark brown solid. This was purified by flash column chromatography using dichloromethane/petroleum spirit (1:3) as the eluting solvent. The compound was obtained pure as a pale yellow solid.

Yield 86%. K: 100° C., $Col_h$:>300° C.,I: Found: C, 80.2; H, 9.6. $C_{126}H_{174}O_{12}$ requires C, 80.4; H, 9.4; O, 10.2%); IR(Nujol): 2360 cm$^{-1}$ (C=C);); $^1H$ NMR (300 MHz, $CDCl_3$, 25° C., TMS): δ=0.93 (t, $^3J(H,H)$=7 Hz, 18H; 6×—$CH_3$), 0.98 (t, $^3J(H,H)$=7 Hz, 18H; 6×—$CH_3$), 1.42 (m, 24H; 6×$CH_2)_2$—), 1.43 (M, 24h; 6×—$(CH_2)_2$—), 1.97 (M, 24H; 6×2—$CH_2CH_2CH_2$—OAr), 2.02 (m, 24H; 6×2×—$CH_2CH_2CH_2$—OAr), 4.22 (t, $^3J(H,H)$=7 Hz, 12H; 6×—$CH_2CH_2$—OAr), 4.34 (t, $^3J(H,H)$=7 Hz, 12H; 6×$CH_2CH_2$—OAr), 7.55 (s, 6H: hexabenztrinaphthylene $C_{1,10,11,20,21,30}$), 8.21 (S, 6H; hexabenztrinaphthylene $C_{5,6,15,16,25,26}$); $^{13}C$ NMR (75 MHz, $^1H${BB} and DEPT, $CDCl_3$, 25° C., TMS): δ=14.54 (2×$CH_3$), 23.18 (2×$CH_2$), 26.47 ($CH_2$), 26.70 ($CH_2$), 30.02 ($CH_2$), 30.35 ($CH_2$), 32.29 ($CH_2$), 32.45 ($CH_2$), 69.60 ($CH_2$), 69.82 ($CH_2$), 107.14 (CH, phenyl $C_2$), 108.17 9CH, phenyl $C_5$), 117.12 (CH triphenylene $C_{1,4,5,8,9,12}$), 124.05 (C, phenyl $C_1$), 124.96 (CH, phenyl $C_6$), 128.31 (C, triphenylene $C_{2,3,6,7,10,11}$), 128.45 (C, triphenylene $C_{4a,4b,8a,8b,12b}$), 149.30 (C, phenyl $C_4$), 150.22 (C, phenyl $C_3$); MS (FAB+): m/z(%): 1885(1) [M+], 424(15), 305(10), 176(30), 55(100).

EXAMPLE 11
2,3,6,7,10,11-hexakis(4-n-nonylphenyl)dipyrazino[2,3-f:2'3'-h]-quinoxaline Yield 10%. M.p. 71° C. and 82° C. Found: C, 84.9; H, 9.4. $C_{102}H_{136}N_6$ requires C, 84.5; H, 9.5; N, 5.8%; IR (Nujol): v~=2360(C=C), 1913 cm$^{-1}$ (C=N); $^1H$ NMR (300 MHz, $CCl_3$, 25° C., TMS): δ=0.90 (T, $^3J(H,H)$=7 Hz, 18H; 6×—$CH_3$), 1.31 (m, 72H; 6×—$(CH_2)_6$), 1.59 (m, 12H, 6×—$CH_2CH_2$—Ar), 2.73 (t, $^3J(H,H)$=7 Hz, 12H; 6×—$CH_2CH_2$—Ar), 7.20 (d, $^3J(H$—$H)$=8.02 Hz, 12H; 6×2CH), 7.145 (D, $^3J(H$—$H)$=8.02 Hz, 12H; 6×2CH); $^{13}C$ NMR (75 MHz, $^1H${BB} and DEPT, $CDCl_3$, 25° C., TMS): δ=14.52 ($CH_3$), 23.08 ($CH_2$, 29.60 ($CH_2$), 29.73 ($CH_2$), 29.92 ($CH_2$), 29.99 ($CH_2$), 31.63 ($CH_2$), 32.30 ($CH_2$), 36.21 ($CH_2$), 128.86 (phenyl CH), 136.55 (quinoxaline $C_{2a,2b,6a,a6b,10a,10b}$), 139.51 (phenyl C), 144.76 (phenyl C), 154.28

(quinoxaline $C_{2,3,6,7,10,11}$); MS (FAB+): m/z(%): 1448(100) [M$^+$], 1348(44), 1248(15), 204(30).

EXAMPLE 12

2,3,6,7,10,11-hexakis-(3,4-dihexyloxyphenyl)dipyrazino[2,3-f.2'3'-h]quinoxaline

Yield 66%. $K_1$: 98° C., $K_2$: 147° C., Col$_1$:194° C., I:.Found: C, 75.95; H, 9.4; N, 4.35%. $C_{120}H_{174}N_6O_{12}$ requires C, 76.2; H, 9.3; $N_6O_{12}$ requires C, 76.2; H, 9.3; N, 4.4; O, 10.1%); IR (Nujol): v~= and (C—H aliph); $^1$H NMR (300 MHz, CDCl$_3$, 25° C., TMS): δ=0.91 (t, $^3$J(H,H)=7 Hz, 18H; 6×-Me), 0.92 (t, $^3$J(H,H)=7 Hz, 18H; 6×-Me), 1.34 (m, 24H; 6×—(CH$_2$)$_2$—), 1.35 (m, 24H; 6×—(CH$_2$)$_2$—), 1.46 (m, 24H; 12×—CH$_2$CH$_2$—OAr), 1.75 (t, $^3$J(H,H)=7H$_2$, 12H; 6×—CH$_2$CH$_2$—OAr), 1.85 (t, $^3$J(H,H)=7 Hz, 12H; 6×—CH$_2$CH$_2$—OAr), 6.88 (d, $^3$J(H,H)=8.02 Hz, 6H; 6×CH, phenyl C$_5$), 7.45 (d, $^4$J(H,H)=2.01 Hz, 6H; 6×CH, phenyl C$_6$), 7.51 (dd, $^3$J(H,H)=2.00 Hz, 6H ×CH, phenyl C$_2$); $^{13}$C NMR (75 MHz, $^1$H{BB} and DEPT, CDCl$_3$, 25° C., TMS); δ=14.00 (12×CH$_3$), 22.60 (12×CH$_2$), 25.70 (12× CH$_2$), 29.15 (6×CH$_2$), 29.19 (6×CH$_2$), 29.15 (6×CH$_2$), 29.20 (6×CH$_2$), 31.6 (12×CH$_2$), 69.15 (6×CH$_2$) 69.24 (6×CH$_2$), 113.12 (phenyl CH), 115.72 (phenyl CH), 123.35 (phenyl CH), 131.47 (phenyl C), 138.68 (quinoxaline $C_{3a,3b,7a,7b,11a,11b}$), 148.72 (phenyl C), 150.39 (phenyl C), 154.28 (quinoxaline $C^{1,2,5,6,9,10}$); MS 9FAB+):m/z(%):1892(10) [M$^+$+2].

EXAMPLE 13

2-(1,4,7-Trioxaoctyl)-3,6,7,10,11-pentahexyloxytriphenylene

A mixture of 2-hydroxy-3,6,7,10,11-pentahexyloxytriphenylene (0.37 g, 0.5 mmol), 1-bromo-2-(2-methoxyethoxy)ethane (0.37 g) and potassium carbonate (0.4 g, 3 mmol) in ethanol (10 ml) was heated under reflux for 72 hours. After which time, it was filtered, extracted with dichloromethane (25 ml), concentrated in vacuo, and the product isolated by column chromatography (silica gel eluting with ethyl acetate) and recrystallised from ethanol to give the title compound as a white solid (0.06 g, 14%, K→D 55.4° C., D→I 69.3° C.). Elemental Analysis: C, 74.95; H, 9.55. $C_{53}H_{82}O_8$ requires: C, 75.14; H, 9.75. Mass Spectrum: m/z (FAB) 869 ([M+23]$^+$, 100%); 846 (M$^+$, 94.5%). $^1$H-NMR: δ$_H$ (CDCl$_3$) 0.93 (15H, t, J=6.7 Hz, O(CH$_2$)$_5$CH$_3$), 1.10–1.70 (30H, m, OCH$_2$CH$_2$(CH$_2$)$_3$), 1.94 (10H, m, OCH$_2$CH$_2$), 3.41 (3H, s, OCH$_2$CH$_2$OCH$_2$CH$_2$CH$_3$), 3.61 (2H, t, J=5.0 Hz, OCH$_2$CH$_2$OCH$_2$CH$_2$), 3.82 (2H, t, J=5.0 Hz, OCH$_2$CH$_2$OCH$_2$), 4.00 (2H, t, J=5.0 Hz, OCH$_2$CH$_2$), 4.23 (10H, t, J=6.5 Hz, OCH$_2$), 4.42 (2H, t, J=5.0 Hz, OCH$_2$), 7.83 (5H, s, ArH), 7.90 (1H, s, ArH).

EXAMPLE 14

2,7-Di(1,4,7-trioxaoctyl)-3,6,10,11-tetrahexyloxytriphenylene was prepared as above from 2,7-dihydroxy-3,6,10,11-tetrahexyloxytriphenylene as a white solid (0.79 g, 61%, mp 44.2° C.). Elemental Analysis: C, 72.35; H, 9.25. $C_{52}H_{80}O_{10}$ requires: C, 72.19; H, 9.32. Mass Spectrum: m/z (EI) 864 (M$^+$,100%). $^1$H-NMR: δ$_H$ (CDCl$_3$) 0.93 (12H, t, J=6.7 Hz, O(CH$_2$)$_5$CH$_3$), 1.10–1.70 (24H, m, OCH$_2$CH$_2$(CH$_2$)$_3$), 1.94 (8H, m, OCH$_2$CH$_2$), 3.41 (6H, s, OCH$_2$CH$_2$OCH$_2$CH$_2$CH$_3$), 3.61 (4H, t, J=5.0 Hz, OCH$_2$CH$_2$OCH$_2$CH$_2$), 3.82 (4H, t, J=5.0 Hz, OCH$_2$CH$_2$OCH$_2$), 4.00 (4H, t, J=5.0 Hz, OCH$_2$CH$_2$), 4.23 (8H, t, J=6.5 Hz, OCH$_2$), 4.42 (4H, t, J=5.0 Hz, OCH$_2$), 7.83 (4H, s, ArH), 7.90 (2H, s, ArH).

EXAMPLE 15

2,7,10-Tri(1,4,7-trioxaoctyl)-3,6,11-trihexyloxytriphenylene was prepared as above from 2,7,10-trihydroxy-3,6,11-trihexyloxytriphenylene as a white solid (0.26 g, 60%, mp 36.5° C.). Elemental Analysis: C, 69.2; H, 8.75. $C_{52}H_{78}O_{12}$ requires: C, 69.36; H, 8.90. Mass Spectrum: m/z (EI) 882, (M$^+$,100%). $^1$H-NMR: δ$_H$ (CDCl$_3$) 0.93 (9H, t, J=6.7 Hz, O(CH$_2$)$_5$CH$_3$),1.10–1.70 (18H, m, OCH$_2$CH$_2$(CH$_2$)$_3$), 1.94 (6H, m, OCH$_2$CH$_2$), 3.41 (9H, s, OCH$_2$CH$_2$OCH$_2$CH$_2$CH$_3$), 3.61 (6H, t, J=5.0 Hz, OCH$_2$CH$_2$OCH$_2$CH$_2$), 3.82 (6H, t, J=5.0 Hz, OCH$_2$CH$_2$OC H$_2$), 4.00 (6H, t, J=5.0 Hz, OCH$_2$CH$_2$), 4.23 (6H, t, J=6.5 Hz, OCH$_2$), 4.42 (6H, t, J=5.0 Hz, OCH$_2$), 7.83 (3H, s, Ar H), 7.90 (3H, s, ArH).

EXAMPLE 16

2-Hydroxy-3,6,7,10,11-pentahexyloxytriphenylene a) 2-Hexyloxyphenol

Catechol (35.0 g, 0.32 mol), potassium carbonate (109.0 g, 0.79 mol) and 1-bromohexane (52.5 g, 0.32 mol) were added to ethanol (300 ml) and heated under reflux for 48 h. After cooling, dichloromethane (300 ml) was added and the solid residues removed by filtration. The solvents were then removed in vacuo and the crude product was purified by column chromatography on silica gel to give title compound (17.9 g, 29%) as a colourless liquid. Found: C, 73.90; H, 9.20. $C_{12}H_{18}O_2$ requires C, 74.19; H, 9.34. δ$_H$ (CHCl$_3$) 6.95–6.83 (m, 4H, ArH), 5.66 (s, 1H, OH), 4.04 (t, J 7, 2H, ArOCH$_2$), 1.89–1.79 (m, 2H, ArOCH$_2$CH), 1.55–1.35 (m, 6H, CH$_2$), 0.95 (t, J 7, 3H, CH$_2$CH$_3$). MS (FAB), 194 (M$^+$, 100%), 110 (45%), 95 (7%), 83 (12%), 69 (9%), 55 (18%).

b) 2-Acetoxy-1-hexyloxybenzene

Acetyl chloride (2.4 g, 30.1 mmol) was added dropwise to vigorously stirred mixture of 2-hexyloxyphenol (5.0 g, 25.8 mmol) and pyridine (5 ml) in dichloromethane (50 ml). The mixture was stirred for 1 hour and poured onto water. The organic layer was separated, dried (MgSO$_4$), concentrated to give crude product which was purified by column chromatography on silica gel using dichloromethane petroleum spirit (1:3) as eluent to give title compound as a colourless oil (5.78 g, 95%). Found: C, 71.00; H, 8.35. $C_{14}H_{20}O_3$ requires C, 71.19; H, 8.47. δ$_H$ (CHCl$_3$) 7.21–7.15 (m, 1H, ArH), 7.05–7.01 (m, 1H, ArH), 6.97–6.89 (m, 2H, ArH), 3.97 (t, J 6.5, 2H, OCH$_2$), 2.30 (s, 3H, COCH$_3$), 1.78–1.71 (m, 2H, ArOCH$_2$CH$_2$), 1.57–1.30 (m, 6H, CH$_2$), 0.90 (t, J 6.9, 3H, CH$_2$CH$_3$). MS (FAB), 236 (M$^+$, 53%), 194 (100%), 153 (27%), 110 (34%), 85 (7%), 55 (7%).

c) 2-Hydroxy-3,6,7,10,11-pentahexyloxytriphenylene

Anhydrous iron chloride (4.7 g, 28.9 mmol) was added to a stirred mixture of 2-acetoxy-1-hexyloxybenzene (3.4 g, 14.4 mmol) and 3,3',4,4'-tetrahexyloxybiphenyl (4.0 g, 7.2 mmol) in dichloromethane. The mixture was stirred for 5 h and poured onto methanol (300 ml). The resultant precipitate was filtered off and saponified with potassium carbonate in ethanol (5% water) under reflux for over night. After cooling, water (50 ml) was added and the product was extracted with dichloromethane, dried (MgSO$_4$), concentrated and purified by column chromatography on silica gel using dichloromethane and petroleum spirit (1:1) as eluent and then recrystallised from ethanol to yield a white solid (3.59 g, 67%). Found: C, 77.30; H, 9.85. $C_{48}H_{72}O_6$ requires C, 77.38; H, 9.74. δ$_H$ (CHCl$_3$) 7.96 (s, 1H, ArH), 7.83–7.82 (m, 4H, ArH), 7.77 (s, 1H, ArH), 5.92 (1H, s, OH), 4.31–4.18 (m, 10H, OCH$_2$), 1.99–1.92 (m, 10H, CH$_2$), 1.58–1.55 (m, 10H, CH$_2$), 1.46–1.38 (m, 20H, CH$_2$), 0.97–0.83 (15H, m, CH$_3$).

EXAMPLE 17

Acetic Acid 2-hydroxy-3,6,7,10,11-pentahexyloxytriphenylene Ester

Acetic acid 2-hydroxy-3,6,7,10,11-pentahexyl-oxytriphenylene ester (7) can be separated before the saponification step in the preparation of (6) as a white solid. Found: C, 76.20; H, 9.60. $C_{50}H_{74}O_7$ requires C, 76.30; H, 9.48. $\delta_H$ (CHCl$_3$) 8.08 (s, 1H, ArH), 7.86 (d, 2H, J 4.0, ArH), 7.82 (d, 2H, J 2.6, ArH), 7.77 (1H, s, ArH), 4.26–4.19 (m, 10H, OCH$_2$), 2.41 (s, 3H, OCOCH$_3$), 1.98–1.86 (m, 10H, CH$_2$), 1.58–1.57 (m, 10H, CH$_2$), 1.42–1.32 (m, 20H, CH$_2$), 0.96–0.88 (m, 15H, CH$_3$). MS (EI), 786 (M$^+$, 89%), 744 (82%), 660 (11%), 491 (5%), 407 (7%), 324 (5%), 295 (10%), 43 (100%).

EXAMPLE 18
Hexanoic Acid 2-hydroxy-3,6,7,10,11-pentahexyloxytriphenylene Ester Hexanoyl chloride (0.10 g, 0.78 mmol) was added to 2-hydroxy-3,6,7,10,11-pentahexyloxytriphenylene (0.29 g, 0.39 mmol) in pyridine (1 ml). The reaction mixture was stirred for 3 hours at room temperature. Water (5 ml) was then added and the product was extracted with dichloromethane, dried (MgSO$_4$), concentrated, and purified by column chromatography on silica gel using dichloromethane and petroleum spirit (1:1) as eluent and then recrystallised from ethanol as a white solid (0.26 g, 79%). Found: C, 76.75; H, 9.90. $C_{54}H_{82}O_7$ requires C, 76.92; H, 9.80; $\delta_H$ (CHCl$_3$) 8.07 (s, 1H, ArH), 7.86 (s, 2H, ArH) 7.81 (2H, d J3.0, ArH) 7.77 (1H, s, ArH) 4.26–4.19 (m, 10H, OCH$_2$), 2.67 (2H, t J 7.5, OCH$_2$) 2.02–1.83 (m, 12H, CH$_2$), 1.65–1.35 (m, 34H, CH$_2$), 0.99–0.89 (18H, m, CH$_3$). MS (EI), 842 (M$^+$-1, 100%), 744 (62%), 660 (9%), 491 (6%), 407 (6%), 323 (10%), 99 (12%), 71 (10%).

EXAMPLE 19
Biphenyl-4-carboxylic Acid 2-hydroxy-3,6,7,10,11-pentahexyloxytriphenylene Ester 4-Biphenylcarbonyl chloride (0.17 g, 0.78 mmol) was added to 2-hydroxy-3,6,7,10,11-pentahexyloxytriphenylene (0.29 g, 0.39 mmol) in pyridine (1 ml). The reaction mixture was stirred for 3 h. at room temperature. Water (5 ml) was then added and the product was extracted with dichloromethane, dried (MgSO$_4$), concentrated, and purified by column chromatography on silica gel using dichloromethane and petroleum spirit (1:2) as eluent and then recrystallised from ethanol as a grey solid (0.30 g, 83%). Found: C, 79.45; H, 8.75. $C_{61}H_{80}O_7$ requires C, 79.18; H, 8.71. $\delta_H$ (CHCl$_3$) 8.37 (d, 2H, J 8.4 ArH), 8.23 (s, 1H, ArH) 7.92–7.69 (8H, m, ArH) 7.55–7.36 (4H, m, ArH) 4.28–4.18 (m, 10H, OCH$_2$), 1.98–1.87 (m, 8H, CH$_2$), 1.83–1.70 (2H, m, CH$_2$), 1.62–1.15 (m, 30H, CH$_2$), 0.98–0.78 (15H, m, CH$_3$). MS (EI), 924 (M$^+$-1, 100%), 744 (61%), 660 (5%), 295 (6%), 181 (89%), 153 (9%).

EXAMPLE 20
4-Nitrobenzoic Acid 2-hydroxy-3,6,7,10,11-pentahexyloxytriphenylene Ester 4-Nitrobenzoyl chloride (0.15 g, 0.81 mmol) was added to 2-hydroxy-3,6,7,10,11-pentahexyloxytriphenylene (0.40 g, 0.54 mmol) in pyridine (1 ml). The reaction mixture was stirred for 3 h. at room temperature. Water (5 ml) was then added and the product was extracted with dichloromethane, dried (MgSO$_4$), concentrated, and purified by column chromatography on silica gel using dichloromethane and petroleum spirit (1:2) as eluent and then recrystallised from ethanol as a yellow solid (0.40 g, 83%). Found: C, 74.0; H, 8.45; N, 1.40. $C_{55}H_{75}NO_9$ requires C, 73.88; H, 8.45; N, 1.57. $\delta_H$ (CHCl$_3$) 8.48 (d, 2H, J 8.6 ArH), 8.41 (d, 2H, J 8.6, ArH) 8.22 (1H, s, ArH) 7.92 (1H, s, ArH), 7.88 (1H, s, ArH), 7.82 (2H, d, J 3, ArH), 7.79 (1H, m, ArH), 4.28–4.18 (m, 10H, OCH$_2$), 1.98–1.92 (m, 8H, CH$_2$), 1.78–1.70 (2H, m, CH$_2$), 1.62–1.10 (m, 30H, CH$_2$), 0.98–0.78 (15H, m, CH$_3$).); MS (FAB), 895 (M$^+$+1, 32%), 880 (11%), 811 (12%), 747 (14%), 660 (9%) 311 (94%), 150 (100%).

EXAMPLE 21
3,5-Dinitrobenzoic Acid 2-hydroxy-3,6,7,10,11-pentahexyloxytriphenylene Ester 3,5-Dinitrobenzoyl chloride (0.17 g, 0.75 mmol) was added to 2-hydroxy-3,6,7,10,11-pentahexyloxytriphenylene (0.28 g, 0.38 mmol) in pyridine (1 ml). The reaction mixture was stirred for 3 h. at room temperature. Water (5 ml) was then added and the product was extracted with dichloromethane, dried (MgSO$_4$), concentrated, and purified by column chromatography on silica gel using dichloromethane and petroleum spirit (1:2) as eluent and then recrystallised from hexane as a yellow solid (0.30 g, 85%). Found: C, 70.45; H, 8.10; N, 2.70. $C_{55}H_{74}N_2O_{11}$ requires C, 70.34; H, 7.94; N, 2.98. $\delta_H$ (CHCl$_3$) 9.36 (s, 2H, ArH), 9.24 (s, 1H, ArH), 8.26 (1H, s, ArH) 7.92 (1H, s, ArH), 7.88 (1H, s, ArH), 7.83 (1H, s, J 3, ArH), 7.82 (1H, s, ArH), 7.78 (1H, s, ArH), 4.28–4.18 (m, 10H, OCH$_2$), 2.02–1.92 (m, 8H, CH$_2$), 1.87–1.75 (2H, m, CH$_2$), 1.69–1.18 (m, 30H, CH$_2$), 0.99–0.81 (15H, m, CH$_3$). MS (EI), 938 (M$^+$-1, 27%), 878 (41%), 744 (52%), 660 (9%), 415 (10%), 149 (100%).

EXAMPLE 22
4-Cyanobenzoic Acid 2-hydroxy-3,6,7,10,11-pentahexyloxytriphenylene Ester 4-Cyanobenzoyl chloride (0.10 g, 0.59 mmol) was added to 2-hydroxy-3,6,7,10,11-pentahexyloxytriphenylene (0.22 g, 0.29 mmol) in pyridine (1 ml). The reaction mixture was stirred for 3 h. at room temperature. Water (5 ml) was then added and the product was extracted with dichloromethane, dried (MgSO$_4$), concentrated, and purified by column chromatography on silica gel using dichloromethane and petroleum spirit (2:1) as eluent and then recrystallised from ethanol as a pale yellow solid (0.22 g, 87%). Found: C, 77.20; H, 8.70; N, 1.60. $C_{56}H_{75}NO_7$ requires C, 76.94; H, 8.65; N, 1.60. $\delta_H$ (CHCl$_3$) 8.41 (d, 1H, J 1.9, ArH), 8.39 (d, 1H, J 1.9, ArH), 8.20 (s, 1H, ArH), 7.91 (s, 1H, ArH), 7.87 (s, 2H, ArH), 7.86–7.83 (3H, m, ArH), 7.78 (s, 1H, ArH), 4.28–4.18 (m, 10H, OCH$_2$), 1.99–1.89 (m, 8H, CH$_2$), 1.78–1.73 (2H, m, CH$_2$), 1.57–1.52 (m, 10H, CH$_2$), 1.44–1.35 (m, 16H, CH$_2$), 1.25–1.17 (m, 4H, CH$_2$), 0.96–0.85 (m, 12H, CH$_3$). 0.81 (3H, t, J 7.2, CH$_3$).); MS (FAB), 874 (M$^+$, 100%), 789 (12%), 744 (21%), 660 (8%), 322 (7%).

EXAMPLE 23
4-Fluorobenzoic Acid 2-hydroxy-3,6,7,10,11-pentahexyloxytriphenylene Ester 4-Fluorobenzoyl chloride (0.09 g, 0.59 mmol) was added to 2-hydroxy-3,6,7,10,11-pentahexyloxytriphenylene (0.22 g, 0.29 mmol) in pyridine (1 ml). The reaction mixture was stirred for 3 h. at room temperature. Water (5 ml) was then added and the product was extracted with dichloromethane, dried (MgSO$_4$), concentrated, and purified by column chromatography on silica gel using dichloromethane and petroleum spirit (2:1) as eluent and then recrystallised from ethanol as a white solid (0.21 g, 85%). Found: C, 76.05; H, 8.95. $C_{55}H_{75}FO_7$ requires C, 76.18; H, 8.72. $\delta_H$ (CHCl$_3$) 8.34–8.30 (m, 2H, ArH), 8.20 (s, 1H, ArH), 8.91–8.79 (m, 5H, ArH), 7.26–7.20 (m, 2H, ArH), 4.27–4.17 (m, 10H, OCH$_2$), 1.98–1.90 (m, 8H, CH$_2$), 1.79–1.72 (2H, m, CH$_2$), 1.59–1.50 (m, 10H, CH$_2$), 1.44–1.35 (m, 16H, CH$_2$), 1.25–1.17 (m, 4H, CH$_2$), 0.96–0.85 (m, 12H, CH$_3$). 0.81 (3H, t, J 7.2, CH$_3$).); MS (EI), 866 (M$^+$-1, 62%), 782 (5%), 744 (14%), 123 (100%), 95 (11%).

EXAMPLE 24
1-Naphthoic Acid 2-hydroxy-3,6,7,10,11-pentahexyloxytriphenylene Ester 1-Naphthoyl chloride (0.09 g, 0.46 mmol) was added to 2-hydroxy-3,6,7,10,11-pentahexyloxytriphenylene (0.17 g, 0.23 mmol) in pyridine (1 ml). The reaction mixture was stirred for 3 h. at room temperature. Water (5 ml) was then added and the product was extracted with dichloromethane, dried ($MgSO_4$), concentrated, and purified by column chromatography on silica gel using dichloromethane and petroleum spirit (1:2) as eluent and then recrystallised from ethanol as a grey solid (0.16 g, 80%). Found: C, 78.55; H, 8.95. $C_{59}H_{78}O_7$ requires C, 78.80; H, 8.74. $\delta_H$ ($CHCl_3$) 9.11 (d, J 8.1, 1H, ArH), 8.59 (d, J 7.3, 1H, ArH), 8.26 (1H, s, ArH) 8.13 (1H, d, J 8.1 ArH), 7.97–7.82 (5H, m, ArH), 7.66–7.59 (4H, m, ArH), 4.28–4.18 (m, 10H, $OCH_2$), 2.17–1.92 (m, 8H, $CH_2$), 1.90–1.77 (2H, m, $CH_2$), 1.58–1.10 (m, 30H, $CH_2$), 0.97–0.81 (12H, m, $CH_3$). 0.75 (3H, t, J 7.0 $CH_3$); MS (EI), 898 ($M^+$–1, 100%), 744 (27%), 658 (6%), 279 (8%), 155 (90%).

EXAMPLE 25
2-Naphthoic Acid 2-hydroxy-3,6,7,10,11-pentahexyloxytriphenylene Ester 2-Naphthoyl chloride (0.13 g, 0.67 mmol) was added to 2-hydroxy-3,6,7,10,11-pentahexyloxytriphenylene (0.25 g, 0.34 mmol) in pyridine (1 ml). The reaction mixture was stirred for 3 h. at room temperature. Water (5 ml) was then added and the product was extracted with dichloromethane, dried ($MgSO_4$), concentrated, and purified by column chromatography on silica gel using dichloromethane and petroleum spirit (1:2) as eluent and then recrystallised from ethanol as a pale yellow solid (0.24 g, 81%). mp 162° C. Found: C, 78.70; H, 8.75. $C_{59}H_{78}O_7$ requires C, 78.80; H, 8.74. $\delta_H$ ($CHCl_3$) 8.91 (s, 1H, ArH), 8.31–8.28 (m, 2H, ArH), 8.06–7.82 (m, 7H, ArH), 7.67–7.60 (m, 3H, ArH), 4.28–4.18 (m, 10H, $OCH_2$), 1.98–1.92 (m, 8H, $CH_2$), 1.89–1.73 (2H, m, $CH_2$), 1.58–1.10 (m, 30H, $CH_2$), 0.97–0.81 (12H, m, $CH_3$). 0.71 (3H, t, J 7.0 $CH_3$); MS (EI), 898 ($M^+$–1, 79%), 744 (36%), 323 (6%), 273 (9%), 155 (100%).

EXAMPLE 26
1,4-difluoro-2,3,6,7,10,11-hexakis(hexyloxy)triphenylene a) 1,4-difluoro,2-hexyloxybenzene 2,5-Difluorophenol (23 g, 0.172 mol) was dissolved in dry, distilled ethanol (300 ml) under a stream of nitrogen. 1-Bromohexane (31.75 g, 0.193 mol, 1.2 eq) and potassium carbonate (133 g, 0.964 mol, 5.5 eq) were added and the reaction mixture was stirred vigorously under reflux for 4 days. Dichloromethane (300 ml) was added to the straw coloured mixture, which was then filtered through a bed of celite to remove the potassium carbonate. The filtrate was washed with water (3×100 ml), and dried with magnesium sulphate. Removal of the solvent in vacuo yields 34.07 g of pale brown oil. This was distilled under reduced pressure to yield a colourless oil (29.22 g, 77%), bp 70° C. @ 0.7 mmHg; (Found: C, 67.35; H, 7.55. $C_{12}H_{16}OF_2$ requires C, 67.3; H, 7.53; O, 7.47; F, 17.76%); $v_{max}$(film)/$cm^{-1}$ 3090 (C—H unsat.), 2932 (C—H aliph.), 1832 (C=C); $\delta_H$(300 MHz; $CDCl_3$) 0.90 (3H, t, $^3J(H,H)$=7 Hz, —$CH_3$), 1.33 (4H, m, 2×—$CH_2$—), 1.35 (2H, septet, $^3J(H,H)$=7 Hz, —$CH_2CH_2CH_2O$—Ar), 1.81 (2H, quintet, $^3J(H,H)$=7 Hz, —$CH_2CH_2CH_2O$—Ar), 3.98 (2H, t, $^3J(H,H)$=7 Hz, —$CH_2CH_2O$—Ar), 6.56 (H, dddd, $^3J(H,F)$=10.8, $^4J(H,F)$=5.3, $^4J(H,H)$=2.4, $^5J(H,H)$=0.7 Hz, $C_6H$), 6.67 (H, dddd, $^3J(H,F)$=10.8, $^3J(H,H)$=9.0, $^4J(H,F)$=5.3, $^4J(H$—$H)$=2.4 Hz, $C_4H$), 6.99 (H, dddd, $^3J(H,F)$=10.8, $^3J(H,H)$=9.0, $^4J(H,F)$=5.3, $^5J(H,H)$=0.7 Hz, $C_3H$); m/z 214 ($M^+$, 19%), 130 ($M^+$-alkoxy chain, 100%), 43 (56%).

b) 1,4-difluoro,2-hexyloxybenzene-1-boronic Acid 1,4-Difluoro-2-hexyloxybenzene (29.22 g, 0.137 mol) was stirred in tetrahydrofuran (150 ml) under anhydrous conditions. The solution was cooled to –78° C. under a stream of dry nitrogen and butyl-lithium (1.6M in hexanes, 81 ml, 0.129 mol) was added drop-wise via cannular over 60 minutes. Stirring was continued for 3 hours at –78° C. The reaction was then quenched (at –78° C. over 30 min) with a solution of trimethylborate (13.23 g, 0.129 mol) in tetrahydrofuran (200 ml). The cooling bath was then removed, and the reaction mixture was stirred overnight at room temperature overnight.

Upon addition of hydrochloric acid (10%, 90 ml) the white suspension dissolved to produce a straw coloured solution. Stirring was continued for 1 hour and then the tetrahydrofuran was removed in vacuo to yield a colourless oil which crystallised rapidly, forming white crystals (49 g). These crystals were dissolved in ether (250 ml), washed with water (3×100 ml) and dried with magnesium sulphate. Removal of the solvent yielded white crystals of the title compound (48 g), which were used without further purification.

c) 3,6-difluoro-2-hexyloxyphenol

White crystals of 1,4-difluoro-2-hexyloxybenzene-1-boronic acid (48 g) were dissolved in warm toluene (150 ml) and hydrogen peroxide (43 ml, 30%) was added drop-wise. Heating was continued for 45 min at 100° C. Once the solution had cooled to room temperature water was added (50 ml) and the layers were separated. The toluene layer was washed with ferrous ammonium sulphate (10%, 2×50 ml) and water (2×50 ml). The combined organic extracts were dried with magnesium sulphate, filtered and the solvent was removed to yield crude 3,6-difluoro,2-hexyloxyphenol as a pale yellow oil (31.67 g, 100%). The crude product was dissolved in toluene (150 ml), extracted with sodium hydroxide solution (10%w/v in methanol, 3×50 ml). The purple, aqueous extract, containing the phenoxide anion of the product, was then re-acidified with concentrated HCl until all of the colour had been displaced (pH~4). The phenol was then extracted with dichloromethane (3×100 ml), washed with water (3×50 ml), dried with magnesium sulphate and filtered. Removal of the solvent in vacuo yielded the required product as an orange/brown oil (27.2 g, 87%). Kugelrohr distillation was performed under reduced pressure (2 mbar), the colourless distillate collected when the oven temp was 100° C. was found to contain only 4 (26.5 g, 82%), (Found: C, 62.65; H, 6.9. $C_{12}H_{16}O_2F_2$ requires C, 62.6; H, 6.9; O, 13.91; F, 16.52%); $v_{max}$(film)/$cm^{-1}$ 3524 and 2932 (C—H aliph), 2300 (C=C); $\delta_H$(300 MHz; $CDCl_3$) 0.90 (3H, t, $^3J(H,H)$=7 Hz, —$CH_3$), 1.32 (4H, m, 2×—$CH_2$—), 1.34 (2H, septet, $^3J(H,H)$=7 Hz, —$CH_2CH_2CH_2O$—Ar), 1.76 (2H, quintet, $^3J(H,H)$=7 Hz, —$CH_2CH_2CH_2O$—Ar), 4.17 (2H, t, $^3J(H,H)$=7 Hz, —$CH_2CH_2O$—Ar), 5.70 (1H, s, —OH, removed with $D_2O$), 6.58 (1H, ddd, $^3J(H,F)$=13.3, $^3J(H,H)$=7.4, $^4J(H,F)$=4.5 Hz, $C_3H$), 6.74 (1H, ddd, $^3J(H,F)$=18.3, $^3J(H,H)$ 7.4, $^4J(H,F)$=4.6 Hz, $C_4H$); $\delta_C$(75 MHz $^1H\{BB\}$, INEPT; $CDCl_3$) 14.31 ($CH_3$), 22.91 ($CH_2$), 25.78 ($CH_2$), 30.34 ($CH_2$), 31.87 ($CH_2$), 74.90 ($CH_2$), 106.65 (CH, dd, $^2J(C,F)$=15.1, $^3J(C,F)$=8.4 Hz, $C_4$), 110.75 (CH, dd, $^2J(C,F)$=15.1, $^3J(C,F)$=8.4 Hz, $C_5$), 135.67 (C, dd, $^2J(C,F)$=15.1, $^3J(C,F)$=8.4 Hz, $C_1$), 138.42 (C, dd, $^2J(C,F)$=15.1, $^3J(C,F)$=8.4 Hz, $C_2$), 147.65 (C, dd, $^1J(C,F)$=239, $^4J(C,F)$=2.6 Hz, $C_6$), 151.7 (C, dd, $^1J(C,F)$=248, $^4J(C,F)$=2.6 Hz, $C_3$); m/z 230 ($M^+$, 10%), 146 ($M^+$-alkoxy chain, 100%), 43 (50%).

d) 1,4-difluoro-2,3-dihexyloxybenzene 3,6-Difluoro-2-hexyloxyphenol (25 g, 0.11 mol) was dissolved in dry, distilled ethanol (350 ml) under a stream of nitrogen. 1-Bromohexane (45.35 g, 0.275 mol, 2.2 eq) and potassium carbonate (75.1 g, 0.54 mol, 5.5 eq) were added and the reaction mixture was stirred vigorously under reflux for 2 days. Dichloromethane (300 ml) was added to the orange reaction mixture, which was then filtered through a bed of celite to remove the potassium carbonate. The filtrate was washed with water (3×100 ml), and dried with magnesium sulphate. Removal of the solvent in vacuo yields 24.07 g of pale brown oil. This was distilled under reduced pressure to yield a colourless oil (18.82 g, 80%), bp 102° C., 0.2 mbar; (Found: C, 68.8; H, 9.05. $C_{18}H_{28}O_2F_2$ requires C, 68.76; H, 8.98; O, 10.18; F, 12.08%); $v_{max}$(film)/cm$^{-1}$ 2956 and 2860 (C—H aliph), 2361 (C≡C); $\delta_H$(300 MHz; CDCl$_3$) 0.90 (3H, t, $^3$J(H,H)=7 Hz, —CH$_3$), 1.33 (4H, m, 2×—CH$_2$—), 1.46 (2H, septet, $^3$J(H,H)=7 Hz, —CH$_2$CH$_2$CH$_2$O—Ar), 1.76 (2H, quintet, $^3$J(H,H)=7 Hz, —CH$_2$CH$_2$CH$_2$O—Ar), 4.08 (2H, t, $^3$J(H,H)=7 Hz, —CH$_2$CH$_2$O—Ar), 6.73 (2H, dd, $^3$J(H,F)=14.5, $^4$J(H,F)=7.2 Hz, $C_{5,6}$H); $\delta_C$(75 MHz $^1$H{BB}, INEPT; CDCl$_3$) 14.41 (CH$_3$), 23.01 (CH$_2$), 25.87 (CH$_2$), 30.45 (CH$_2$), 31.98 (CH$_2$), 74.99 (CH$_2$), 110.15 (CH, dd, 2J(C,F)=17.7, $^3$J(C,F)=4.3 Hz, $C_{5,6}$), 141.94 (C, dd, $^2$J(C,F)=11.0, $^3$J(C,F)=7.0 Hz, $C_{2,3}$), 153.12 (C, dd, $^1$J(C,F)=244.2, $^4$J(C,F)=3.6 Hz, $C_{1,4}$); m/z (FAB+); 314 (M$^+$, 99%), 146 (M$^+$-alkoxy chains, 100%), 85 (79), 55 (40%).

e) 2,5-difluoro-3,4-dihexyloxybenzene-1-boronic Acid 1,4-Difluoro-2,3-dihexyloxybenzene (11.2 g, 0.036 mol) was stirred, under nitrogen, in anhydrous tetrahydrofuran (150 ml). The reaction mixture was cooled to −78° C. and then butyl lithium (1.6M in hexanes, 24.38 ml, 0.039 mol) was added via cannular over one hour. Stirring was continued at −78° C. for 2 hours. This temperature was maintained whilst a solution of trimethylborate (4.05 g, 0.039 mol) in dry tetrahydrofuran (100 ml) was added drop-wise. The cooling bath was then removed and the reaction was stirred overnight at room temperature. Addition of HCl (1M, 36 ml) dissolved the white suspension and a yellow solution was formed. Extraction was performed with toluene (2×100 ml), the combined organics extracts were then washed with water (2×50 ml), dried with magnesium sulphate. Removal of the drying agent by filtration and the solvent in vacuo yielded a brown oil containing the crude product (11.95 g, 93%). The product was used in the next step without further purification.

f) Pinacol Ester of 2,5-difluoro-3,4-dihexyloxybenzene-1-boronic Acid

The crude 2,5-difluoro-3,4-dihexyloxybenzene-1-boronic acid (11.95 g as brown oil) was dissolved in tetrahydrofuran (10 ml). Concentrated sulphuric acid (3 drops) and pinacol (3.92 g, 0.033 mol) were then added and the solution was heated to reflux overnight under a protective dry nitrogen atmosphere. The cool solution was filtered to remove any insoluble impurities and the solvent was removed in vacuo to yield a brown oil. TLC analysis was hampered due to the product spreading and sticking to the silica, purification was affected by Kugelrohr distillation. The title compound was obtained as a colourless, viscous oil (8.1 g, 51%), oven temp 150° C., 0.2 mbar (Found: C, 65.6; H, 8.7. $C_{24}H_{39}BF_2O_4$ requires C, 65.46; H, 8.93; B, 2.45; F, 8.63; O, 14.53%); $v_{max}$(film)/cm$^{-1}$ 2932 (C—H aliph), 2359 (C≡C), 1371 (B—O); $\delta_H$(300 MHz; CDCl$_3$) 0.90 (6H, t, $^3$J(H,H)=7 Hz, 2×—CH$_3$), 1.35 (8H, m, 4×—CH$_2$—), 1.46 (4H, septet, $^3$J(H,H)=7 Hz, 2×—CH$_2$CH$_2$CH$_2$O—Ar), 1.75 (4H, quintet, $^3$J(H,H)=7 Hz, 2×—CH$_2$CH$_2$CH$_2$O—Ar), 4.06 (2H, t, $^3$J(H,H)=7 Hz, —CH$_2$CH$_2$O—Ar), 4.14 (2H, t, $^3$J(H,H)=7 Hz, —CH$_2$CH$_2$O—Ar), 6.58 (H, dd, $^3$J(H,F)=9.9, $^4$J(H,F)=5 Hz, $C_6$H); $\delta_C$(75 MHz $^1$H{BB}, INEPT; CDCl$_3$) 14.42 (CH$_3$), 22.99 (CH$_2$), 25.16 (CH$_3$, pinacol), 25.83 (CH$_2$), 30.47 (CH$_2$), 31.98 (CH$_2$), 74.90 (CH$_2$), 84.42 (C, pinacol), 116.25 (CH, dd, $^2$J(C,F)=20.14, $^3$J(C,F)=9.6 Hz, $C_6$), 141.44 (C, dd, $^2$J(C,F)=15.6, $^3$J(C,F)=4.0 Hz, $C_3$), 144.71 (C, dd, $^2$J(C,F)=13.2, $^3$J(C,F)=5.0 Hz, $C_4$), 152.3 (C, d, $^1$J(C,F)=246.1 Hz, $C_2$), 157.4 (C, d, $^1$J(C,F)=248.17; m/z 440 (M$^+$, 12%), 272 (M$^+$—both alkyl chains, 57%), 212 (65%), 43 (100%).

g) 3,4,-dibromo-1,2-dihexyloxybenzene 1,2-Dihexyloxybenzene (35 g, 0.126 mol) was stirred in anhydrous dichloromethane (250 ml) at 0° C. to which was added iron powder (1 g, cat) and iodine (0.5 g, cat). The reaction vessel was fitted with a trap containing sodium hydroxide and nitrogen was bubbled through the reaction mixture to remove the HBr produced. Elemental bromine (50 g, 0.314 mol, 2.5 eq) in dichloromethane (250 ml) was added drop wise from an addition funnel over 2 hours, the temperature being maintained at 0° C. After addition was complete, stirring was continued at room temperature overnight. Saturated sodium metabisulphate solution (200 ml) was added and the product was extracted with dichloromethane (2×250 ml). The combined organic extracts were washed with water (2×100 ml), dried with magnesium sulphate and filtered. Removal of the solvent in vacuo yields a brown oil. Filtration through a short silica column using 1:1 toluene:dichloromethane as eluant removed the coloured impurities. The solvent was removed in vacuo to yield 3,4-dibromo-1,2-dihexyloxybenzene as a colourless oil (45.9 g, 95%); (Found: C, 50.1; H, 6.4. $C_{18}H_{28}O_2Br_2$ requires: C, 49.7; H, 6.47; O, 7.34; Br, 36.63%); $v_{max}$(film)/cm$^{-1}$ 2931 and 2859 (C—H aliph), 2360 (C≡C), 652 (C—Br); $\delta_H$(300 MHz; CDCl$_3$) 0.90 (6H, t, $^3$J(H,H)=7 Hz, 2×—CH$_3$), 1.33 (8H, m, 4×—CH$_2$—), 1.45 (4H, septet, $^4$J(H,H)=7 Hz, 2×—CH$_2$CH$_2$CH$_2$O—Ar), 1.77 (4H, quintet, $^3$J(H,H)=7 Hz, 2×—CH$_2$CH$_2$CH$_2$O—Ar), 3.91 (4H, t, $^3$J(H,H)=7 Hz, 2×—CH$_2$CH$_2$O—Ar), 7.06 (2H, s); $\delta_C$(75 MHz $^1$H{BB}, INEPT; CDCl$_3$) 14.42 (CH$_3$), 22.99 (CH$_2$), 26.01 (CH$_2$), 29.50 (CH$_2$), 31.92 (CH$_2$), 69.82 (CH$_2$), 115.03 (C, $C_{4,5}$), 118.29 (CH, $C_{3,6}$), 149.40(C, $C_{1,2}$); m/z 436 (M$^+$, 16%), 352 (M$^+$—$C_6H_{12}$, 11%), 268 (M$^+$−2×$C_6H_{12}$, 85%), 43 (100%).

h) 3',6'-difluoro-3,4,4',5',3'',4''-hexakishexyloxyl[1,1':2',1''] terphenyl 1,2-Dibromo-3,6-difluoro-4,5-dihexyloxybenzene (0.5 mmol.) and Pd(PPh$_3$)$_4$ (3 mol % Pd(0), per bromine atom) were stirred in degassed DME (50 ml) under argon. The pinacol boronate ester (3,4-dihexyloxybenzene boronic acid, 1.5 mmol) was dissolved in toluene, degassed, and after about 15 minutes was added to the reaction by cannular. A suspension of barium hydroxide (1.5 mmol.) in water (2.5 ml) was degassed and added directly to the reaction. The reaction was carried out under argon at 80° C., for 21 hours, and then allowed to cool, water was added. The mixture was extracted with ether, the extracts were washed with saturated sodium chloride solution (2×50 ml), water (2×50 ml), dried (Na$_2$SO$_4$), and the solvent removed in vacuo to leave a red, viscous oil (~80%). This was subjected to column chromatography on silica gel using petroleum ether/ethyl acetate as the eluting solvent (using a gradient of 9:1 initially to 4:1 finally) (Found: C, 74.65; H, 9.8. $C_{54}H_{84}O_6F_2$ requires: C, 74.79; H, 9.76; O, 11.07; F, 4.38%); $v_{max}$(film)/cm$^{-1}$ 2931 and 2859 (C—H aliph), 2360 (C≡C); $\delta_H$(300 MHz; CDCl$_3$) 0.9048 (18H, t, J=7 Hz, 9×-Me), 1.3340 (36H, m, 18×—CH$_2$—), 1.5664 (4H, quint, J=7 Hz, 2×—CH$_2$CH$_2$CH$_2$O—Ar), 1.6672 (4H, quint, J=7 Hz, 2×—CH$_2$CH$_2$CH$_2$O—Ar), 1.7906 (4H, quint, J=7 Hz, 2×—CH$_2$CH$_2$CH$_2$O—Ar), 3.6982 (4H, t, J=7 Hz, 2×—CH$_2$CH$_2$O—Ar), 3.9253 (4H, t, J=7 Hz, 2×—CH$_2$CH$_2$O—Ar), 4.1342 (4H, t, J=7 Hz, 2×—CH$_2$CH$_2$O—Ar), 6.5294 (H$_c$, 2H, d, J=1.181 Hz, coupled: p to H$_a$), 6.6261 (H$_a$, 2H, dd, J=8.235, 1.81 Hz, coupled: o to H$_b$, m to H$_c$); $\delta_C$(75 MHz $^1$H{BB}, INEPT; CDCl$_3$) 14.43 (6×CH$_3$), 23.04 (6×CH$_2$), 26.08 (2×CH$_2$), 26.12 (4×CH$_2$), 29.47 (2×CH$_2$), 29.65 (4×CH$_2$), 30.55 (2×CH$_2$), 31.99 (2×CH$_2$), 32.03 (2×CH$_2$), 69.36 (2×CH$_2$OAr), 69.51 (2×CH$_2$OAr), 75.20 (2×CH$_2$OAr) 113.07 (CH, s, $C_{2,2''}$), 117.11(CH, s, $C_{6,6''}$), 123.83 (C, s, $C_{5,5''}$), 124.48 (C, dd, $^2$J$_{F—C}$=10.5 Hz, $^3$J$_{F—C}$=9.5 Hz, $C_{1',2'}$), 126.03 (C, s, $C_{1,1''}$), 140.83 (CF, dd, $^1J_{F-C}$=12 Hz, $^4J_{F-C}$=7.5 Hz, $C_{3',6'}$), 148.63 (C, s, $C_{4,4''}$), 148.69 (C, s, $C_{3,3''}$), 151.92 (C, s (low intensity), $C_{4',5'}$); m/z (FAB+) 867 (M$^+$, 100%).

i) 1,4-difluoro-2,3,6,7,10,11-hexakis(hexyloxy)triphenylene

The terphenyl of example 26 h) (0.5 mmol) was stirred in dry dichloromethane (50 ml). Iron (III) chloride (1 mmol) was weighed and added to the reaction flask under an inert atmosphere. The reaction mixture turned a deep green colour and was stirred at room temperature until no starting material remained (TLC (1:1 dichloromethane/petroleum spirit) on small portions following methanol work up). The reaction mixture was worked up by pouring onto methanol (anhydrous, 50 ml). To the resulting, brown solution, was added water (50 ml) and dichloromethane (50 ml). The layers were extracted with dichloromethane, washed with ferrous ammonium sulphate (5% solution, 50 ml) and water (2×50 ml). Drying over magnesium sulphate, filtration and removal of solvent in vacuo yielded a red to purple solid. The purple solid was dissolved in dichloromethane and filtered through a bed of silica, removal of solvent yielded a sticky off-white solid. The product was recrystallised from ethanol and dried in glass (Yield >85%). The melting point of the solid was below room temperature (Found: C, 74.7; H, 9.7;. $C_{54}H_{84}O_6F_2$ requires: C, 74.96; H, 9.76; O, 11.07; F, 4.38%); $\delta_H$(300 MHz; CDCl$_3$) 0.9286 (18H, t, J=7 Hz, 6×-Me), 1.380 (24H, m, 12×—CH$_2$—), 1.57 (12H, m, 6×—CH$_2$CH$_2$CH$_2$O—Ar), 1.860 (4H, quint, J=7 Hz, 2×—CH$_2$CH$_2$CH$_2$O—Ar), 1.918 (8H, quint, J=7 Hz, 4×—CH$_2$CH$_2$CH$_2$O—Ar), 4.19 (4H, t, J=7 Hz, 2×—CH$_2$CH$_2$O—Ar), 4.224 (8H, t, J=7 Hz, 4×—CH$_2$CH$_2$O—Ar), 7.81 (H$_b$, 2H, s), 8.47 (H$_a$, 2H, t, J=3.01 Hz, nOe coupling to $^{19}$F); 14.07 (6×CH$_3$), 22.66 (6×CH$_2$), 25.58 (2×CH$_2$), 25.81 (4×CH$_2$), 29.23 (2×CH$_2$), 29.33 (4×CH$_2$), 30.21 (2×CH$_2$), 31.66 (2×CH$_2$), 31.68 (2×CH$_2$), 69.06 (2×CH$_2$OAr), 69.50 (2×CH$_2$OAr), 75.14 (2×CH$_2$OAr) 106.70 (CH, s, $C_{8,9}$), 111.43 (CH, m, nOe coupling to $^{19}$F, $C_{5,12''}$), 115.49 (C, m, $C_{4b,12b}$), 120.68 (C, s, $C_{4b,12a}$), 124.84 (C, s, $C_{8a,8b}$), 139.44 (C, m, $C_{2,3}$), 148.53 (C, s, $C_{7,10}$), 149.14 (C, s, $C_{6,11}$), 152.40 (C, m, (low intensity), $C_{1,4}$); m/z (FAB+) 866 (M$^+$, 100%).

What is claimed is:

1. A mixture comprising a molecule of formula I;

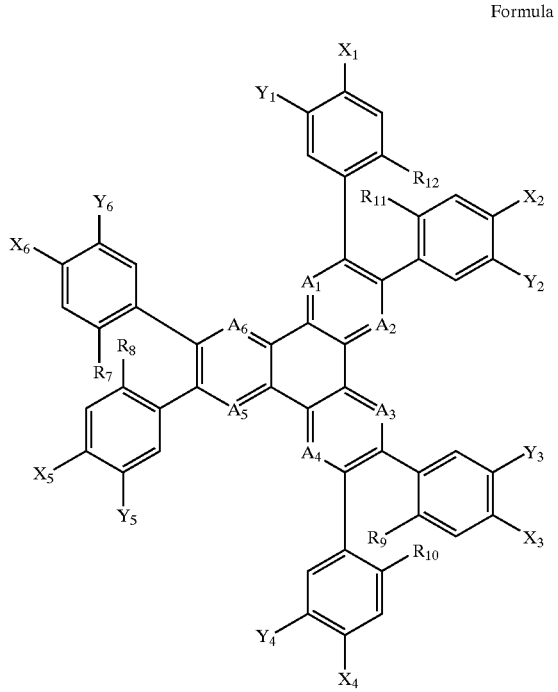

Formula I in which $A_1$, $A_2$, $A_3$, $A_4$, $A_5$ and $A_6$, are each selected from the group consisting of N and —CH;

$Y_1$, $Y_2$, $Y_3$, $Y_4$, $Y_5$ and $Y_6$, are each selected from the group consisting of hydrogen and $C_1$ to $C_{12}$ alkoxy;

$X_1$, $X_2$, $X_3$, $X_4$, $X_5$ and $X_6$, are each selected from the group consisting of hydrogen, $C_1$ to $C_{12}$ alkoxy and alkyl $C_1$ to $C_{12}$; and $R_7$, $R_8$, $R_9$, $R_{10}$, $R_{11}$ and $R_{12}$ are each hydrogen, or each of $R_7$ and $R_8$, $R_9$ and $R_{10}$ and $R_{11}$ and $R_{12}$ may form a bond;

and a molecule of formula II;

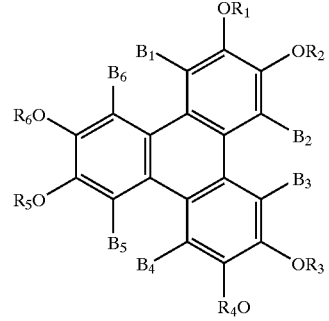

Formula II in which $R_1$, $R_2$, $R_3$, $R_4$, $R_5$ and $R_6$, are each selected from the group consisting of alkyl or substituted (and/or chiral) alkyl $C_1$ to $C_{16}$, acyl $C_1$ to $C_{16}$, polyethyleneoxy, a flexible connection to a polymer backbone or part of a polymer backbone in homopolymers, copolymers and block copolymers; and $B_1$, $B_2$, $B_3$, $B_4$, $B_5$ and $B_6$, are each selected from the group consisting of hydrogen, alkyl $C_1$ to $C_{16}$, alkoxy $C_1$ to $C_{16}$, nitro, halogeno, cyano, amido, diazo and ester.

2. A mixture according to claim 1 characterised in that in the compound of formula I each of $A_1$, $A_2$, $A_3$, $A_4$, $A_5$ and $A_6$ are the same.

3. A mixture according to claim 2 characterised in that each of $A_1$, $A_2$, $A_3$, $A_4$, $A_5$ and $A_6$ is N, and each of $Y_1$, $Y_2$, $Y_3$, $Y_4$, $Y_5$ and $Y_6$ represents hydrogen or alkoxy $C_3$ to $C_8$.

4. A mixture according to claim 2 characterised in that each of $A_1$, $A_2$, $A_3$, $A_4$, $A_5$ and $A_6$ is N, and each of $X_1$, $X_2$, $X_3$, $X_4$, $X_5$ and $X_6$ is $C_2$ to $C_{12}$ alkyl or $C_4$ to $C_{12}$ alkoxy.

5. A mixture according to claim 4 characterised in that each of $X_1$, $X_2$, $X_3$, $X_4$ $X_5$ and $X_6$ is $C_6$ to $C_9$ alkyl or $C_6$ to $C_9$ alkoxy.

6. A mixture according to claim 5 characterised in that each of $X_1$, $X_2$, $X_3$, $X_4$, $X_5$ and $X_6$ is either $C_9$ alkyl or $C_6$ alkoxy.

7. A mixture according to claim 6 characterised in that each of $X_1$, $X_2$, $X_3$, $X_4$, $X_5$ and $X_6$ is the same $C_9$ alkyl or each of $X_1$, $X_2$, $X_3$, $X_4$, $X_5$ and $X_6$ is the same $C_6$ alkoxy.

8. A mixture according to claim 4 characterised in that each of $Y_1$, $Y_2$, $Y_3$, $Y_4$, $Y_5$ and $Y_6$ is hydrogen and each of $X_1$, $X_2$, $X_3$, $X_4$, $X_5$ and $X_6$ is $C_9$ alkyl.

9. A mixture according to claim 4 characterised in that each of $Y_1$, $Y_2$, $Y_3$, $Y_4$, $Y_5$ and $Y_6$ is $C_6$ alkoxy and each of $X_1$, $X_2$, $X_3$, $X_4$, $X_5$ and $X_6$ is $C_6$ alkoxy.

10. A mixture according to claim 1 characterised in that each of $A_1$, $A_2$, $A_3$, $A_4$, $A_5$ and $A_6$ is C—H and each of $Y_1$, $Y_2$, $Y_3$, $Y_4$, $Y_5$ and $Y_6$ is hydrogen or alkoxy $C_3$ to $C_8$.

11. A mixture according to claim 10 characterised in that each of $Y_1$, $Y_2$, $Y_3$, $Y_4$, $Y_5$ and $Y_6$ is hydrogen or alkoxy $C_5$ to $C_7$.

12. A mixture according to claim 11 characterised in that each of $Y_1$, $Y_2$, $Y_3$, $Y_4$, $Y_5$ and $Y_6$ is hydrogen or alkoxy $C_6$.

13. A mixture according to claim 1 characterised in that each of $A_1$, $A_2$, $A_3$, $A_4$, $A_5$ and $A_6$ is C—H, and each of $X_1$, $X_2$, $X_3$, $X_4$, $X_5$ and $X_6$ is $C_2$ to $C_{12}$ alkyl or $C_2$ to $C_{12}$ alkoxy.

14. A mixture according to claim 1 characterised in that each of $X_1$, $X_2$, $X_3$, $X_4$, $X_5$ and $X_6$ is $C_6$ to $C_{12}$ alkoxy.

15. A mixture according to claim 1 characterised in that the compounds of formula I are compounds of formula III;

Formula III

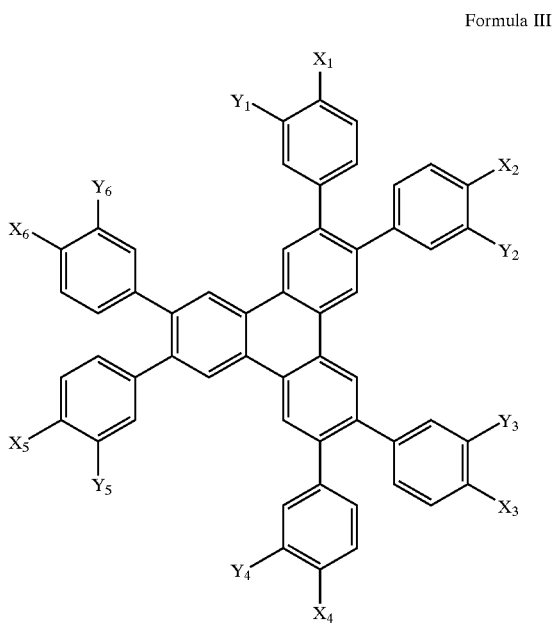

in which $X_1, X_2, X_3, X_4, X_5$ and $X_6$ are each the same and are selected from the group consisting of —$C_9H_{19}$, —$C_{12}H_{25}$, —$OC_6H_{13}$ and —$OC_{11}H_{23}$; and
each of $Y_1, Y_2, Y_3, Y_4, Y_5$ and $Y_6$ are each the same and are selected from the group consisting of hydrogen and —$OC_6H_{13}$.

16. A mixture according to claim 1 characterised in that compounds of formula I are compounds of formula IV;

Formula IV

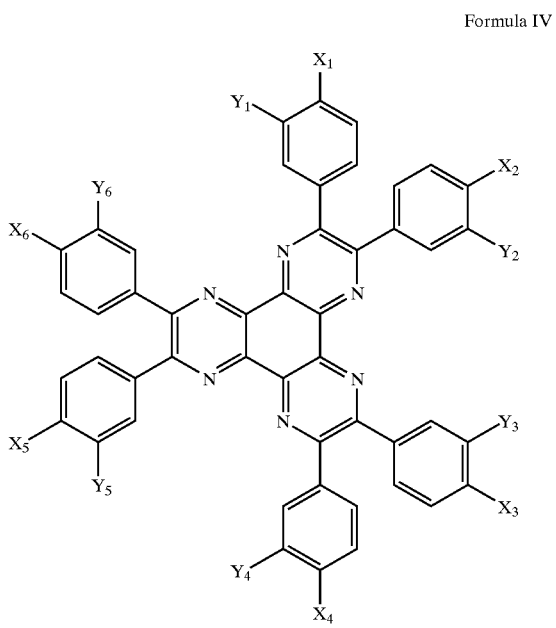

in which $X_1, X_2, X_3, X_4, X_5$ and $X_6$ are each the same and are selected from the group consisting of —$C_9H_{19}$, and —$OC_6H_{13}$; and
each of $Y_1, Y_2, Y_3, Y_4, Y_5$ and $Y_6$ are each the same and are selected from the group consisting of hydrogen and —$OC_6H_{13}$.

17. A mixture according to claim 1 characterised in that in the molecule of formula II each of $R_1, R_2, R_3, R_4, R_5$ and $R_6$ are the same and $B_1, B_2, B_3, B_4, B_5$ and $B_6$ are hydrogen.

18. A mixture according to claim 17 characterised in that each of $R_1, R_2, R_3, R_4, R_5$ and $R_6$ are alkyl $C_3$ to $C_{16}$.

19. A mixture according to claim 1 characterised in that each of $R_1, R_2, R_3, R_4, R_5$ and $R_6$ are alkyl $C_4$ to $C_{11}$.

20. A mixture according to claim 19 characterised in that each of $R_1, R_2, R_3, R_4, R_5$ and $R_6$ are $C_6$ or $C_{11}$ alkyl.

21. A mixture according to claim 1 characterised in that compounds of formula II are selected from the group consisting of 2,3,6,7,10,11-hexahexyloxytriphenylene and 2,3,6,7,10,11-hexaundecyloxytriphenylene.

22. A mixture according to claim 21 characterised in that the compound of the formula II is 1,4-difluoro-2,3,6,7,10,11-hexahexyloxytriphenylene.

23. A mixture according to claim 1 characterised in that in the compound of formula II in that each of $R_1, R_2, R_3, R_4, R_5$ and $R_6$ are the same and are alkyl $C_3$–$C_{16}$.

24. A mixture according to claim 23 characterised in that each of $R_1, R_2, R_3, R_4, R_5$ and $R_6$ are $C_4$–$C_{11}$ alkyl.

25. A mixture according to claim 1 characterised in that each of $B_1, B_2, B_3,$ and $B_4$ are hydrogen and each of $B_5$ and $B_6$ are each selected from the group consisting of hydrogen and fluorine.

26. A mixture according to claim 1 characterised in that in the compounds of formula II each of $R_1, R_2, R_3, R_4, R_5$ and $R_6$ are selected from the group consisting of alkyl $C_2$–$C_{11}$ or ethyleneoxy $C_3$–$C_9$.

27. A mixture according to claim 26 characterised in that each of $R_1, R_2, R_3, R_4, R_5$ and $R_6$ are the same and are ethyleneoxy $C_5$.

28. A mixture according to claim 26 characterised in that each of $R_1, R_2, R_3, R_4, R_5$ and $R_6$ are a combination of ethyleneoxy $C_5$ and alkyl $C_6$.

29. A mixture according to claim 1 characterised in that the compound of formula II is selected from the group consisting of 2-(1,4,7-Trioxaoctyl)-3,6,7,10,11-pentahexyloxytriphenylene, 2,7-Di(1,4,7-trioxaoctyl)-3,6,10,11-tetrahexyloxytriphenylene, 2,7,10-Tri(1,4,7-trioxaoctyl)-3,6,11-trihexyloxytriphenylene and 2,3,6,7,10,11-Hexa(1,4,7-trioxaoctyl)triphenylene.

30. A mixture according to claim 1 characterised in that the compound of formula II is a side chain substituent in the form shown in formula V;

Formula V

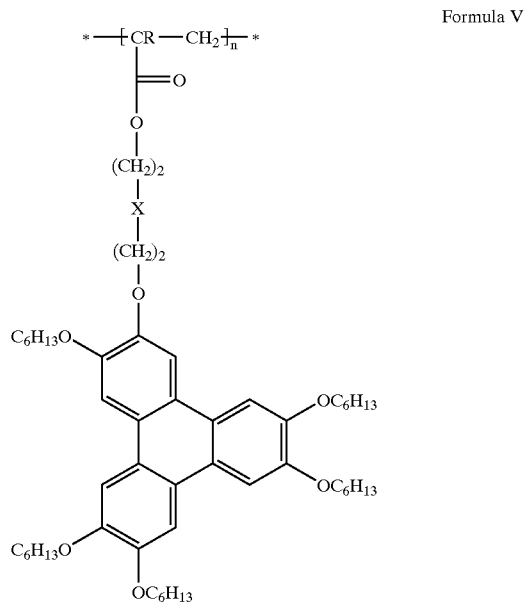

wherein X is alkyl $C_1$–$C_{10}$ or ether oxygen linkage (—O—), and R is hydrogen or methyl.

31. A mixture according to claim 1 characterised in that the compound of formula II as a functionality in polystyrene block copolymers of the form shown in formula VI

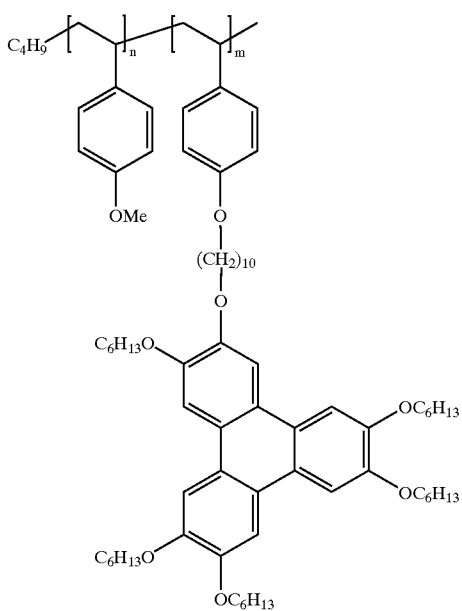

in which the ratio of n:m is from 6–18:1.

32. A mixture according to claim 1 characterised in that the compound of formula I is a constituent part of a polymer backbone of formulae VII, the length of the flexible spacer n is between 6 and 18 and the number of molecules of formula II per polymer formula VII, m, is between 2 and 1000.

Formula VII

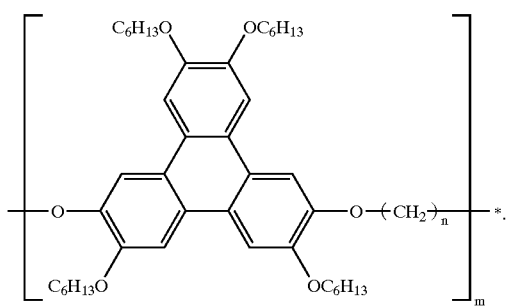

33. A mixture according to claim 1 characterised in that the compound of formula II is part of a block copolymer containing blocks of polyethylene oxide and blocks of formula VII, where the number of molecules of formula I (m) is 10–100 and the number of ethyleneoxide groups in the side chains (n) is 200–500

34. A mixture according to claim 1 characterised in that the compounds of formula I are selected from the group consisting of
2,3,6,7,10,11-hexakis(4-n-nonylphenyl)dipyrazine[2,3-f:2',3'-h]quinoxaline;
2,3,6,7,10,11-hexakis-(3,4-dehexyloxyphenyl)dipyrazino[2,3-f:2',3'-h]quinoxaline;
2,3,6,7,10,11-hexakis-4-(-n-nonylphenyl)-triphenylene;
2,3,6,7,10,11-hexakis-(4-n-dodecylphenyl)triphenylene;
2,3,6,7,10,11-hexakis-(4-n-hexyloxy-phenyl)-triphenylene;
2,3,6,7,10,11-hexakis-(4-n-undecyloxy-phenyl)-triphenylene;
2,3,6,7,10,11-hexakis-(3,4-n-dihexyloxy-phenyl)-triphenylene; and
2,3,8,9,12,13,18,19,22,23,28,29-dodecakis(hexyloxy)hexabenz[a,c,k,m,v,w]trinaphthylene.

35. A mixture according to claim 1 characterised in that the compounds of formula II are selected from the group consisting of
2,3,6,7,10,11-hexahexyloxytriphenylene,
2,3,6,7,10,11-hexaundecyloxytriphenylene,
1,4-difluoro-2,3,6,7,10,11-hexahexyloxytriphenylene,
2-(1,4,7-trioxaoctyl)-3,6,7,10,11-pentahexyloxytriphenylene,
2,7-di(1,4,7-trioxaoctyl)-3,6,10,11-tetrahexyloxytriphenylene,
2,7,10-tri(1,4,7-trioxaoctyl)-3,6,11-trihexyloxytriphenylene,
2,3,6,7,10,11-hexa(1,4,7-trioxaoctyl)triphenylene,
acetic acid 2-hydroxy-3,6,7,10,11-pentahexyloxytriphenylene ester,
hexanoic acid 2-hydroxy-3,6,7,10,11-pentahexyloxytriphenylene ester,
4-biphenylcarboic acid 2-hydroxy-3,6,7,10,11-pentahexyloxytriphenylene ester,
4-nitrobenzoic acid 2-hydroxy-3,6,7,10,11-pentahexyloxytriphenylene ester,
3,5-dinitrobenzoic acid 2-hydroxy-3,6,7,10,11-pentahexyloxytriphenylene ester,
4-cyanobenzoic acid 2-hydroxy-3,6,7,10,11-pentahexyloxytriphenylene ester,
4-fluorobenzoic acid 2-hydroxy-3,6,7, 10,11-pentahexyloxytriphenylene ester,
1-naphthoic acid 2-hydroxy-3,6,7,10,11-pentahexyloxytriphenylene ester,
2-naphthoic acid 2-hydroxy-3,6,7,10,11-pentahexyloxytriphenylene ester,
1,4-difluoro-2,3,6,7,10,11-hexakis(hexyloxy)triphenylene, and
polythenes bearing formula II as a side chain substituent (formula V),
polyacrylates bearing formula II as a side chain substituent (formula VI
polymers containing formula II as part of the polymer backbone (formula VII),
block copolymers containing a central core of polymer with formula II as part of the Formula VIII

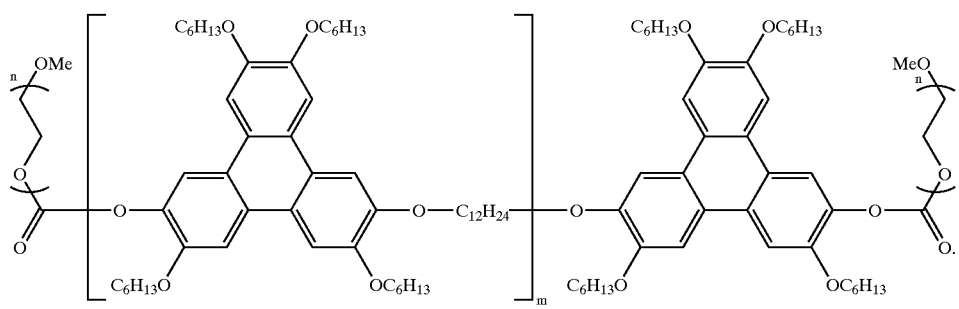

polymer backbone surrounded by blocks of poly(ethyleneoxide) with molecular weights in the range 750–2000 (formula VIII).

36. A mixture according to claim 1 characterised in that the mixture comprises a compound of formula I selected from the group consisting of
2,3,6,7,10,11-hexakis(4-nonylphenyl)dipyrazine[2,3-f:2',3'-h]quinoxaline;
2,3,6,7,10,11-hexakis-(4-nonylphenyl)-triphenylene;
2,3,6,7,10,11-hexakis-(4-dodecylphenyl)triphenylene;
2,3,6,7,10,11-hexakis-(4-hexyloxy-phenyl)-triphenylene;
2,3,6,7,10,11-hexakis-(4-n-undecyloxy-phenyl)-triphenylene;
and a compound of formula II selected from the group consisting of
2,3,6,7,10,11-hexahexyloxytriphenylene,
2,3,6,7,10,11-hexaundecyloxytriphenylene,
1,4-difluoro-2,3,6,7,10,11-hexahexyloxytriphenylene,
2-(1,4,7-trioxaoctyl)-3,6,7,10,11-pentahexyloxytriphenylene,
2,7-di(1,4,7-trioxaoctyl)-3,6,10,11-tetrahexyloxytriphenylene,
2,7,10-tri(1,4,7-trioxaoctyl)-3,6,11-trihexyloxytriphenylene,
2,3,6,7,10,11-hexa(1,4,7-trioxaoctyl)triphenylene,
acetic acid 2-hydroxy-3,6,7,10,11-pentahexyloxytriphenylene ester,
hexanoic acid 2-hydroxy-3,6,7,10,11-pentahexyloxytriphenylene ester,
4-biphenylcarboic acid 2-hydroxy-3,6,7,10,11-pentahexyloxytriphenylene ester,
4-nitrobenzoic acid 2-hydroxy-3,6,7,10,11-pentahexyloxytriphenylene ester,
3,5-dinitrobenzoic acid 2-hydroxy-3,6,7,10,11-pentahexyloxytriphenylene ester,
4-cyanobenzoic acid 2-hydroxy-3,6,7,10,11-pentahexyloxytriphenylene ester,
4-fluorobenzoic acid 2-hydroxy-3,6,7,10,11-pentahexyloxytriphenylene ester,
1-naphthoic acid 2-hydroxy-3,6,7,10,11-pentahexyloxytriphenylene ester,
2-naphthoic acid 2-hydroxy-3,6,7,10,11-pentahexyloxytriphenylene ester,
1,4-difluoro-2,3,6,7,10,11-hexakis(hexyloxy) triphenylene, and
polythenes bearing formula II as a side chain substituent (formula V),
polyacrylates bearing formula II as a side chain substituent (formula VI)
polymers containing formula II as part of the polymer backbone (formula VII),
block copolymers containing a central core of polymer with formula II as part of the
polymer backbone surrounded by blocks of poly(ethyleneoxide) with molecular weights in the range 750–2000 (formula VIII).

37. A mixture according to claim 1 wherein the compound of formula 1 is manufactured by reacting a hexahalotriphenylene or hexahaloquinoxaline with a boronic ester of formula V;

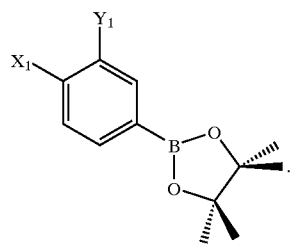

38. A mixture according to claim 1 characterised in that the ratio of the compound of formula I to the compound of formula II is substantially 1:1.

39. A liquid crystal comprising the mixture according to claim 1.

40. A liquid crystal according to claim 39 characterized in that the liquid crystal exhibits a hexagonal columnar phase at a temperature of between less than room temperature and 280° C.

41. A liquid crystal according to claim 39 characterised in that the liquid crystal has an alternating stack structure.

42. A liquid crystal according to claim 41 characterised in that the liquid crystal comprises an alternating stack of compounds of formula I and formula II.

43. A liquid crystal according to claim 39 characterized in that the liquid crystal has enhanced low temperature conductivity.

44. A stacked silicon chip system comprising a liquid crystal with a hexagonal columnar phase at a temperature of between less than room temperature and 280° C. and wherein the liquid crystal comprising a mixture of compounds of formula I and formula II according to claim 1.

45. A conductive layer in a photoreproductive and/or an electrophotographic system comprising a liquid crystal with a hexagonal columnar phase at a temperature of between less than room temperature and 280° C. and wherein the liquid crystal comprising a mixture of compounds of formula I and formula II according to claim 1.

46. An electronic "nose array" comprising a liquid crystal with a hexagonal columnar phase at a temperature of between less than room temperature and 280° C. and wherein the liquid crystal comprising a mixture of compounds of formula I and formula II according to claim 1.

47. A spatial light comprising a liquid crystal with a hexagonal columnar phase at a temperature of between less than room temperature and 280° C. and wherein the liquid crystal comprising a mixture of compounds of formula I and formula II according to claim 1.

48. A composition comprising a molecule of formula I;

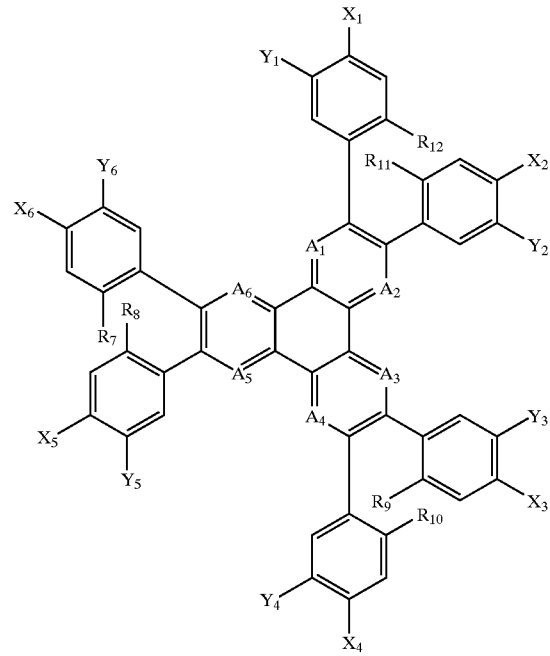

Formula I wherein $A_1, A_2, A_3, A_4, A_5$ and $A_6$, are each selected from the group consisting of N and —CH;
$Y_1, Y_2, Y_3, Y_4, Y_5$ and $Y_6$, are each selected from the group consisting of hydrogen and $C_1$ to $C_{12}$ alkoxy;
$X_1, X_2, X_3, X_4, X_5$ and $X_6$, are each selected from the group consisting of hydrogen, $C_1$ and $C_{12}$ alkoxy or alkyl $C_1$ to $C_{12}$; and
$R_7, R_8, R_9, R_{10}, R_{11}$ and $R_{12}$ are each hydrogen, or each of $R_7$ and $R_8$, $R_9$ and $R_{10}$ and $R_{11}$ and $R_{12}$ may form a bond;
and a molecule of formula II;

Formula II

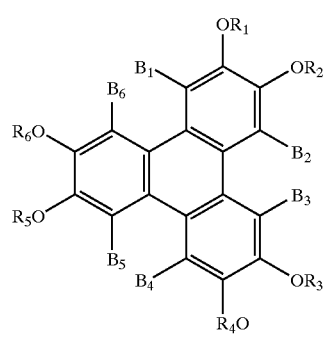

wherein $R_1, R_2, R_3, R_4, R_5$ and $R_6$, are each selected from the group consisting of alkyl or substituted (and/or chiral) alkyl $C_1$ to $C_{16}$, acyl C1 to C16, polyethyleneoxy, a flexible connection to a polymer backbone or part of a polymer backbone in homopolymers, copolymers and block copolymers; and
B1, B2, B3, B4, B5 and B6, are each selected from the group consisting of hydrogen, alkyl $C_1$ to $C_{16}$, alkoxy $C_1$ to $C_{16}$, nitro, halogeno, cyano, amido, diazo and ester.

49. A composition according to claim 48 characterised in that the compounds of formula I are compounds of formula III;

Formula III

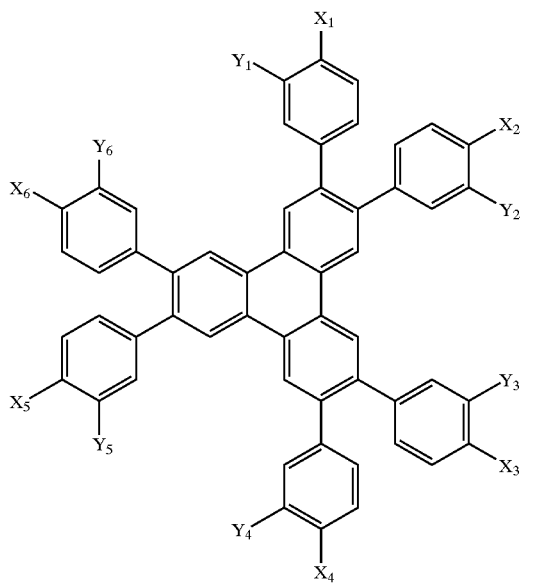

wherein $X_1, X_2, X_3, X_4, X_5$ and $X_6$ are each the same and are selected from the group consisting of —$C_9H_{19}$, —$C_{12}H_{25}$, —$OC_6H_{13}$ and —$OC_{11}H_{23}$; and each of $Y_1, Y_2, Y_3, Y_4, Y_5$ and $Y_6$ are each the same and are selected from the group consisting of hydrogen and —$OC_6H_{13}$.

50. A composition according to claim 48 characterised in that compounds of formula I are compounds of formula IV;

Formula IV

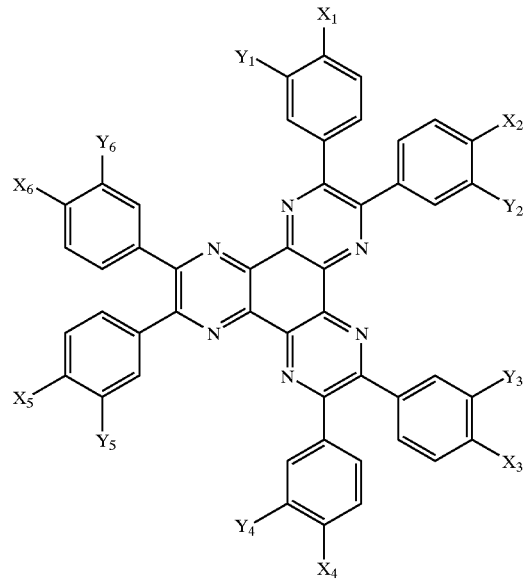

wherein $X_1, X_2, X_3, X_4, X_5$ and $X_6$ are each the same and are selected from the group consisting of —$C_9H_{19}$, and —$OC_6H_{13}$; and
each of $Y_1, Y_2, Y_3, Y_4, Y_5$ and $Y_6$ are each the same and are selected from the group consisting of hydrogen and —$OC_6H_{13}$.

51. A composition according to claim 48 characterised in that the compound of formula II is a side chain substituent in the form shown in formula V;

Formula V

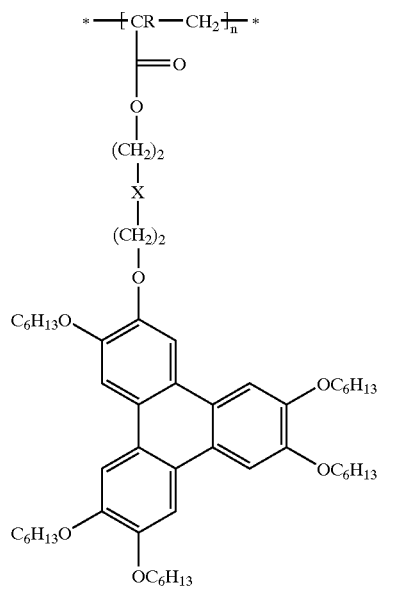

wherein X is alkyl $C_1$–$C_{10}$ or ether oxygen linkage (—O—), and R is hydrogen or methyl.

52. A composition according to claim 48 characterised in that the compound of formula II as a functionality in polystyrene block copolymers of the form shown in formula VI

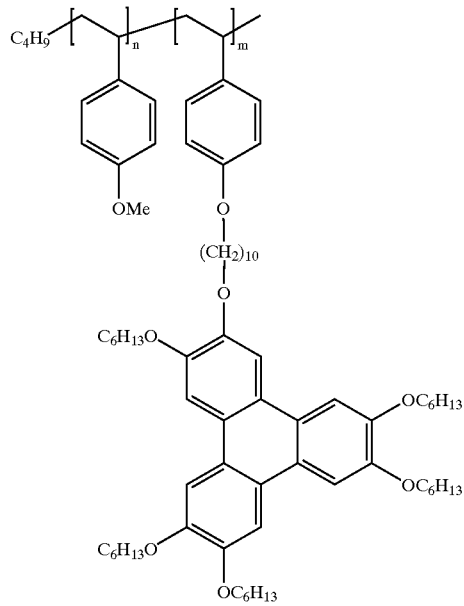

wherein the ratio of n:m is from 6–18:1.

53. A composition according to claim 48 characterised in that the compound of formula I is a constituent part of a polymer backbone of formulae VII, the length of the flexible spacer n is between 6 and 18 and the number of molecules of formula II per polymer formula VII, m, is between 2 and 1000

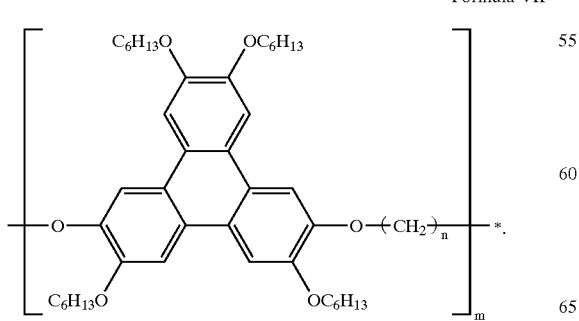

54. A method of manufacturing a mixture and/or a liquid crystal comprising mixing a compound of formula I;

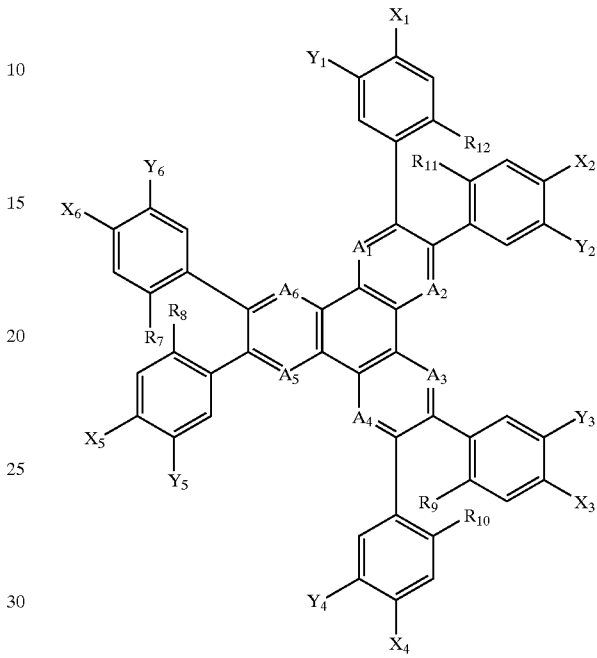

wherein $A_1, A_2, A_3, A_4, A_5$ and $A_6$, are each selected from the group consisting of N and —CH;

$Y_1, Y_2, Y_3, Y_4, Y_5$ and $Y_6$, are each selected from the group consisting of hydrogen and $C_1$ to $C_{12}$ alkoxy;

$X_1, X_2, X_3, X_4, X_5$ and $X_6$, are each selected from the group consisting of hydrogen and $C_1$ to $C_{12}$ alkoxy or alkyl $C_1$ to $C_{12}$; and $R_7, R_8, R_9, R_{10}, R_{11}$ and $R_{12}$ are each hydrogen or each of $R_7$ and $R_8$, $R_9$ and $R_{10}$ and $R_{11}$ and $R_{12}$ may form a bond;

with a compound of formula II;

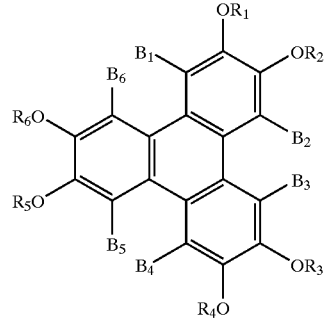

Wherein $R_1$, $R_2$, $R_3$, $R_4$, $R_5$ and $R_6$, are each selected from the group consisting of alkyl or substituted (and/or chiral) alkyl $C_1$ to $C_{16}$, acyl $C_1$ to $C_{16}$, polyethyleneoxy, a flexible connection to a polymer backbone or part of a polymer backbone in homopolymers, copolymers and block copolymers; and $B_1$, $B_2$, $B_3$, $B_4$, $B_5$, and $B_6$, are each selected from the group consisting of hydrogen, alkyl $C_1$ to $C_{16}$, alkoxy $C_1$ to $C_{16}$, nitro, halogeno, cyano, amido, diazo and ester.

55. A method of manufacturing a liquid crystal comprising combining a molecule of formula I;

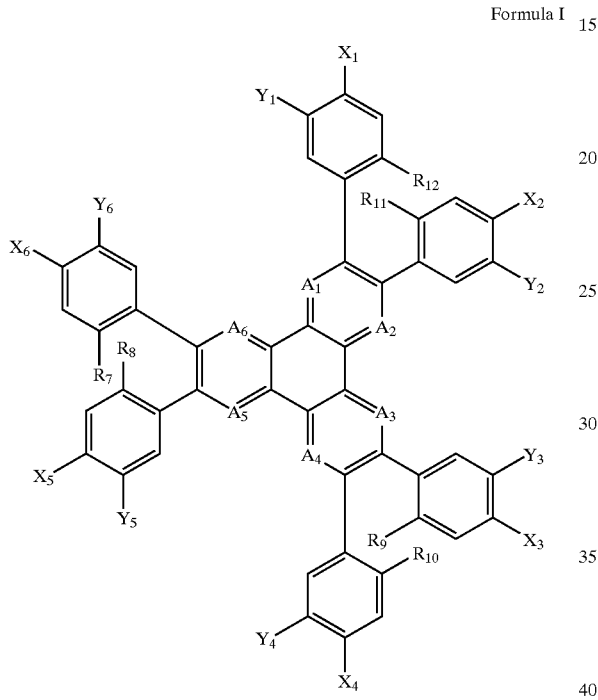

Formula I wherein $A_1$, $A_2$, $A_3$, $A_4$, $A_5$ and $A_6$, are each selected from the group consisting of N and —CH;

$Y_1$, $Y_2$, $Y_3$, $Y_4$, $Y_5$ and $Y_6$, are each selected from the group consisting of hydrogen and $C_1$ to $C_{12}$ alkoxy;

$X_1$, $X_2$, $X_3$, $X_4$, $X_5$ and $X_6$, are each selected from the group consisting of hydrogen, $C_1$ and $C_{12}$ alkoxy or alkyl $C_1$ to $C_{12}$; and $R_7$, $R_8$, $R_9$, $R_{10}$, $R_{11}$ and $R_{12}$ are each hydrogen, or each of $R_7$ and $R_8$, $R_9$ and $R_{10}$ and $R_{11}$ and $R_{12}$ may form a bond;

and a molecule of formula II;

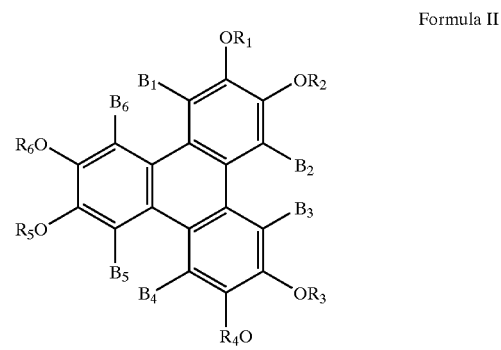

Formula II wherein $R_1$, $R_2$, $R_3$, $R_4$, $R_5$ and $R_6$, are each selected from the group consisting of alkyl or substituted (and/or chiral) alkyl $C_1$ to $C_{16}$, acyl $C_1$ to $C_{16}$, polyethyleneoxy, a flexible connection to a polymer backbone or part of a polymer backbone in homopolymers, copolymers and block copolymers; and $B_1$, $B_2$, $B_3$, $B_4$, $B_5$ and $B_6$, are each selected from the group consisting of hydrogen, alkyl $C_1$ to $C_{16}$, alkoxy $C_1$ to $C_{16}$, nitro, halogeno, cyano, amido, diazo and ester.

* * * * *

UNITED STATES PATENT AND TRADEMARK OFFICE
CERTIFICATE OF CORRECTION

PATENT NO.    : 6,689,290 B2
DATED         : February 10, 2004
INVENTOR(S)   : Boden et al.

It is certified that error appears in the above-identified patent and that said Letters Patent is hereby corrected as shown below:

Column 15,
Line 50, should read -- $^{1}cm^{-1}$. FTIR spectra were recorded on a Perkin-Elmer --

Column 25,
Line 47, should read -- 100 ml. Concentrated sulphuric acid (3 drops) and pinacol --

Signed and Sealed this

Sixth Day of July, 2004

JON W. DUDAS
*Acting Director of the United States Patent and Trademark Office*